US012571764B2

(12) United States Patent
Bohbot et al.

(10) Patent No.: US 12,571,764 B2
(45) Date of Patent: Mar. 10, 2026

(54) RECEPTOR-BASED BIOSENSORS

(71) Applicant: STATE OF ISRAEL, MINISTRY OF AGRICULTURE & RURAL DEVELOPMENT, AGRICULTURAL RESEARCH ORGANIZATION (A.R.O.) (VOLCANI CENTER), Rishon Leziyon (IL)

(72) Inventors: Jonathan Bohbot, Rehovot (IL); Sefi Vernick, Tel Aviv (IL)

(73) Assignee: STATE OF ISRAEL, MINISTRY OF AGRIGULTURE & RURAL DEVELOPMENT, AGRICULTURAL RESEARCH ORGANIZATION (A.R.O.) (VOLCANI CENTER), Rishon Leziyon (IL)

( * ) Notice: Subject to any disclaimer, the term of this patent is extended or adjusted under 35 U.S.C. 154(b) by 516 days.

(21) Appl. No.: 17/905,440

(22) PCT Filed: Mar. 2, 2021

(86) PCT No.: PCT/IL2021/050230
§ 371 (c)(1),
(2) Date: Sep. 1, 2022

(87) PCT Pub. No.: WO2021/176447
PCT Pub. Date: Sep. 10, 2021

(65) Prior Publication Data
US 2023/0091126 A1 Mar. 23, 2023

Related U.S. Application Data

(60) Provisional application No. 62/983,933, filed on Mar. 2, 2020.

(51) Int. Cl.
*G01N 27/414* (2006.01)
*G01N 33/00* (2006.01)

(52) U.S. Cl.
CPC ..... *G01N 27/4141* (2013.01); *G01N 27/4146* (2013.01); *G01N 33/0047* (2013.01)

(58) Field of Classification Search
CPC ........... G01N 27/4141; G01N 27/4145; G01N 27/4146; G01N 33/0047
See application file for complete search history.

(56) References Cited

U.S. PATENT DOCUMENTS 8,481,324 B2 * 7/2013 Haick ................ G01N 33/0034
436/112
11,237,196 B2 2/2022 Morimitsu
(Continued)

FOREIGN PATENT DOCUMENTS

JP        2018059786 A  *  4/2018  ............. G01N 27/00
KR  1020130120960 A  *  11/2013  ........... G01N 27/403
(Continued)

OTHER PUBLICATIONS

EPO machine-generated English language translation of Byeongju et al. KR 10-2013-0120960 (A) , published Nov. 5, 2013 (Year: 2013).*

(Continued)

*Primary Examiner* — Alexander S Noguerola
(74) *Attorney, Agent, or Firm* — FISHERBROYLES, LLP; Roger L. Browdy

(57) ABSTRACT

A bioelectronic sensor is disclosed for detecting presence of at least one volatile organic compound (VOC), the sensor comprising a single carbon nanotube (CNT) covalently immobilizing a single receptor optionally being a mammalian or an insect receptor, wherein association of the VOC to said receptor allows for a measurable electric field effect.

26 Claims, 28 Drawing Sheets

(56) References Cited

U.S. PATENT DOCUMENTS

| | | | | |
|---|---|---|---|---|
| 2006/0055392 A1 * | 3/2006 | Passmore | ............... | B82Y 15/00 |
| | | | | 324/71.1 |
| 2008/0032295 A1 * | 2/2008 | Toumazou | ......... | G01N 27/4145 |
| | | | | 435/287.2 |

FOREIGN PATENT DOCUMENTS

| | | | | | |
|---|---|---|---|---|---|
| KR | 20160066625 A | * | 6/2016 | ........... | C07K 14/435 |
| WO | 2018/116186 A1 | | 6/2018 | | |

OTHER PUBLICATIONS

Wang et al., "Antifungal activity of volatile organic compounds from Streptomyces alboflavus TD-1," FEMS Microbiol Lett 341 (2013) 45-51 (Year: 2013).*

Dayani et al., "Lipid Bilayers Covalently Anchored to Carbon Nanotubes," Langmuir 2012, 28, 8174-8182 (Year: 2012).*

Murugathas et al., "Biosensing with Insect Odorant Receptor Nanodiscs and Carbon Nanotube Field-Effect Transistors," ACS Appl. Mater. Interfaces 2019, 11, 9530-9538 (Year: 2019).*

EPO machine-generated English language translation of Takeuchi et al. JP 2018059786 (A), published Apr. 12, 2018 (Year: 2018).*

Ruel et al., "Supersensitive Odorant Receptor Underscores Pleiotropic Roles of Indoles in Mosquito Ecology," Frontiers in Cellular Neuroscience, Jan. 2019 | vol. 12 | Article 533 (Year: 2019).*

Bohbot et al., "Conservation of Indole Responsive Odorant Receptors in Mosquitoes Reveals an Ancient Olfactory Trait," Chem. Senses 36: 149-160, 2011, with supplementary material (Year: 2011).*

EPO machine-generated translation of Park et al. KR-20160066625-A. original published Jun. 13, 2016 (Year: 2016).*

Richard Glatz et al: "Mimicking nature's noses: From receptor deorphaning to olfactory biosensing", Progress in Neurobiology, Elsevier, Amsterdam, NL, vol. 93, No. 2, Nov. 22, 2010, pp. 270-296.

Khadka Roshan et al: "Synergistic improvement in the performance of insect odorant receptor based biosensors in the presence of Orco", Biosensors and Bioelectronics, Elsevier Science Ltd. UK, Amsterdam, NL, vol. 153, Jan. 23, 2020.

* cited by examiner

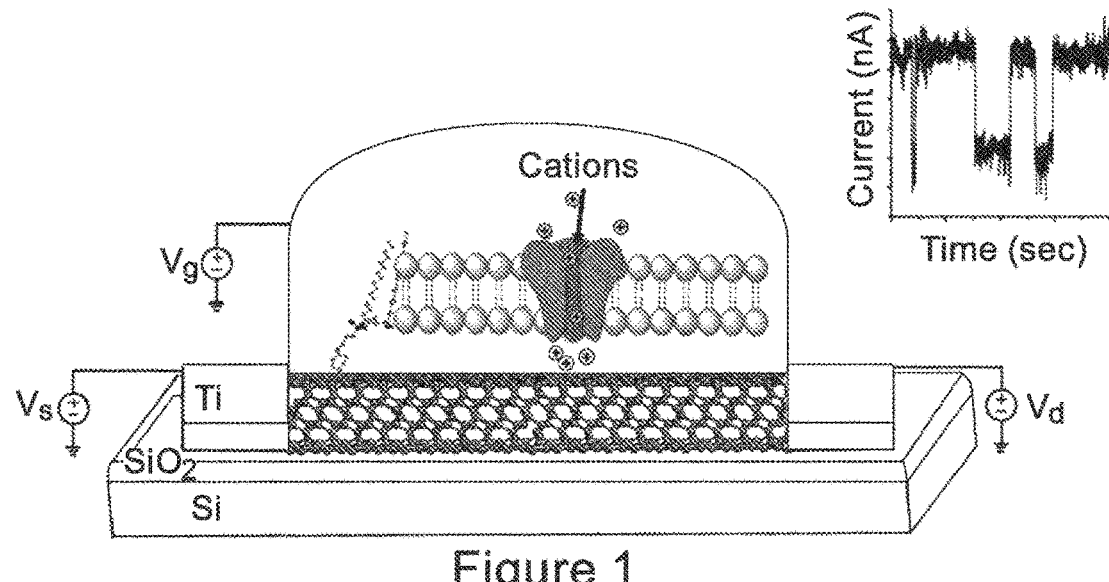
Figure 1
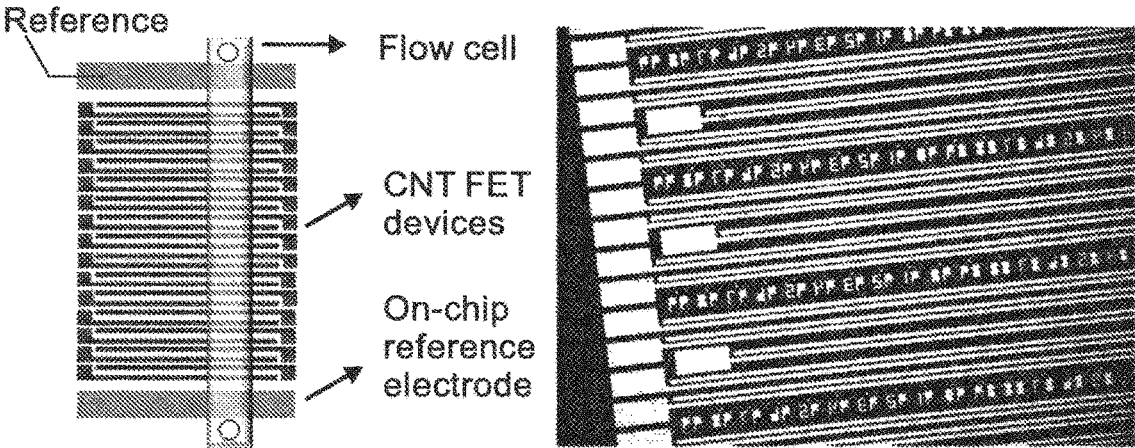
Figure 2A
Figure 2B

VUAA1
Innovapharm Ltd. 382200000

2-4-Octadienal, predominantly *trans*
Sigma W372102

Carvacrol
Sigma W224502

Figure 4A

RECEPTOR-BASED BIOSENSORS

TECHNOLOGICAL FIELD

The invention generally concerns receptor-based biosensors and uses thereof.

BACKGROUND

Indole with its bicyclic and aromatic structure is the simplest and most ubiquitous representative of its chemical class. It is composed of a six-membered benzene ring fused to a five-membered nitrogen-containing pyrrole ring and it is this core scaffold that is the basis of a large variety of natural compounds, such as hormones and synthetic molecules of biomedical importance.

Due to its predominantly hydrophobic aromatic system, indole (and skatole) is sparingly soluble in water. It exhibits a broad range of biological activities across the animal kingdom and acts as a major interspecies signaling molecule. It is synthesized from tryptophan by bacteria, fungi, yeast and plants, and depending on its concentration, has a flowery, mothballs or fecal smell to humans. Indole and its methylated analog-skatole—are widespread in human and animal everyday life. They are released by wine, meat, dairy products, coffee, seafood and many other foodstuffs.

Detection of indole and its derivative skatole are of paramount importance and their diagnostic value is evident across the agro-food chain, environmental indicator, process manufacturing sectors and the clinical arena.

The organoleptic properties of food depend in part on the presence and respective concentrations of indoles. The strong attraction to these compounds has promoted their use as additives in personal care products and flavoring agents (e.g. chocolate, coffee, ice-cream, cigarettes and candies). Indole is a common reagent for the manufacture of perfume, drugs and pesticides. Detecting these compounds is paramount for safety and quality assurance purposes in process manufacturing.

Ensuring food safety and quality is crucial to public health and for limiting food spoilage, respectively. As indicators of decomposition and microbial contamination, indole and skatole have been proposed as quality indicators in marine foodstuff such as crustaceans, fish and oyster. Similarly, indole and skatole may be used as markers of fecal contamination of food.

Pork is one of the fastest growing livestock subsectors and demand is rising steeply particularly in Brazil and China. The presence of the unpleasant odor, the so-called boar taint in pig meat, poses a great risk to the pork supply chain and consumer acceptance is directly dependent on the degree to which it permeates pork meat. Boar taint is perceived as a penetrating "animal", "urine", "fecal" or "sweat" like unpleasant odor. Indole, skatole and androstenone are the main contributors to this malodor. Despite the use of chemical analysis tools and sensory panels to detect some of these compounds, there are currently no satisfying solutions to detect boar taint in the slaughter line that meet the industry speed, sensitivity and selectivity requirements.

Industrial livestock production is a source of environmental odors, which can be detrimental to animals, workers and nearby human populations. Skatole has been associated with a variety of health conditions. At high doses, skatole is a pneumotoxin, causing acute pulmonary edema and emphysema in ruminants and damages the lungs and livers of animals and humans. It is also considered a neurotoxic agent, inducing the degeneration of the olfactory epithelium leading to reversible anosmia in rats. Therefore, skatole may be used as an environmental indicator in farming, in industries relying heavily on this compound such as perfumery or in wastewater treatment plants.

Human, animal and agricultural uses of water are increasing globally. Ensuring that water supplies remain safe for consumption and irrigation purposes is a priority that requires the monitoring of indicator organisms such as coliform bacteria, fecal bacteria, *salmonella* or *Vibrio cholerae*. These indole-producing organisms can, therefore, be monitored using indole and skatole as biomarkers.

Indole is also a characteristic biomarker of foodborne pathogenic *E. coli* (*E. coli* O157: H7) with many reports indicating its high production. Pathogenic foodborne *E. coli* O157: H7 can cause hemorrhagic colitis and hemolytic uremic syndrome, with children being at high risk.

Indole and skatole, along with volatile sulfur compounds are major components of breath odor and halitosis and may be used as clinical markers for the diagnosis of halitosis and underlying etiologies, including metabolic diseases and oral inflammations. Patients with bowel cancer have higher fecal skatole content than healthy individuals suggesting that skatole may be a valuable biomedical marker in this context as well.

The last twenty years have witnessed the discovery of insect receptors beginning with those initially described in *Drosophila melanogaster* followed by those from several mosquito species. Since then, hundreds of insect genomes and several thousand odorant receptor (OR) genes have been annotated representing an unlimited and untapped source of potential biorecognition elements. However, the vast majority of these receptors remains orphan and has no foreseeable use in biosensing. Deorphanized ORs from *D. melanogaster* exhibit various degrees of promiscuity towards high concentrations of compounds of limited interest in biosensing.

The first large-scale deorphanization efforts of mosquito ORs led to the identification of the indole receptor named OR2. The closely related paralog OR10 is a skatole receptor in several mosquito species. OR9, a third member of this gene subgroup was also shown to act as a skatole receptor. Interestingly OR2 and OR9/OR10 exhibit reverse selectivity for the two closely chemical analogs indole and skatole at concentrations that can reach the upper picomolar range based on cell-based assays. These pharmacological features are equivalent or better than those of pheromone receptors, which are the epitome of odorant receptor sensitivity and selectivity. The advantage of indole ORs, as opposed to pheromone receptors, is their selective and sometime specific relationship to indole and skatole, two compounds of significant interests in many research fields and industries.

WO 2018/116186 teaches a sensor device comprising an insect ORx in electrical communication with a substrate, wherein the device is configured to detect a change in an electrical characteristic of the substrate.

PUBLICATIONS

[1] WO 2018/116186

General Description

The ability to detect volatile organic compounds (VOC) with high sensitivity and selectivity offers wide-range applications. The inventors of the technology disclosed herein have realized that such a desirable ability may be offered by peptidic systems, wherein mammalian or other receptors, as disclosed herein, fulfilling the task.

In the exemplified systems disclosed herein, the mosquito-derived indolergic receptor OR9, the most sensitive odorant receptor discovered so far, was incorporated with a CNT-FET device to produce an indole and skatole specific bioelectronic nose. By utilizing well-established protocols for heterologous expression, OR9 was expressed in conjunction with the OR co-receptor (Orco) or alternatively, as a single transmembrane receptor. Purification of the OR9-containing small membrane fragments and further immobilization to the sidewall of a CNT transistor channel, via covalent modification, resulted in an OR9-based CNT-FET bioelectronic nose that is subject of the invention.

The immobilization of OR9, versus Orco-OR9, directly affects signal transduction mechanism and ultimately the final readout. The inclusion of Orco as an integral part of the herein disclosed CNT-FET device results in an overall improved performance. Orco is a dedicated cation channel and should effectively transduce ligand binding. When using a small band-gap semiconducting CNTs, the ligand-induced cation current increases the CNT conductance at positive gate voltage (when electrons are the dominant charge carriers). Cationic charges generally reduce CNT resistance by creating a lower resistance path for electrons. Similarly, a shift in the threshold gate voltage for conduction was observed during a current-gate voltage sweep (I-V). Such a shift reflects a local gating effect due to charges in proximity to the CNT sidewall.

The presence of Orco, however, is not strictly required for bioelectronic sensing. Ligand binding-induced conformational changes of OR9 are sufficient to affect local electric fields in the vicinity of the CNT sidewall resulting in altered conductance. Such sensitivity is attributed to the CNT 1D channel transport kinetics.

Despite the many advantages of bioelectronic sensing, most of the methods and devices developed so far are inherently noisy and suffer from relatively poor selectivity due to non-specific adsorption of organic molecules to the various transducers surfaces. Single-molecule methods possibly alleviate this limitation.

Thus, in its broadest aspect, the invention disclosed herein contemplates use of a receptor, i.e., a cell-associated protein, for the construction of a bioelectronic sensor for detecting presence of at least one volatile organic compound (VOC), the sensor comprising a single carbon nanotube (CNT) covalently immobilizing a single receptor, wherein association/binding/interaction of the VOC allows for a measurable electric field effect.

As used herein, the receptor may be any cell-associated protein or glycoprotein or proteoglycan or other glycans such as gangliosides that is capable of selectively binding to a bioactive molecule. The receptor may be any such protein or fragment thereof that comprises a recognition site capable of selectively binding the VOC.

The receptor may be a mammalian receptor, a bacterial receptor, a fungal receptor, a plant receptor or an insect receptor. Other receptors may also be used. In some embodiments, the receptor is an insect receptor, e.g., derived from winged or wingless insects. Non-limiting examples of insects include mosquitos and flies. In some embodiments, the insect is a mosquito.

The receptor may be selected amongst membrane bound receptor, cytosolic receptors, nuclear receptors, monomeric receptors or multimeric receptors.

Thus, the invention provides a bioelectronic sensor for detecting presence of at least one VOC, the sensor comprising a single carbon nanotube (CNT) covalently immobilizing a single receptor optionally being a mammalian or an insect receptor, wherein association/binding/interaction of the VOC to said receptor allows for a measurable electric field effect.

In some embodiments, the VOC is as least one organic compound having a boiling point less than or equal to 250° C. measured at a standard atmospheric pressure. The VOCs may be selected based on their structure and the presence or absence of one or more functionalities. In some embodiments, the VOCs are selected amongst aliphatic VOCs, aromatic VOCs, carbocyclic VOCs, heterocyclic VOCs, fused ring VOCs, polar VOC, water borne VOCs, air borne VOCs, steroidal VOCs and others.

Non-limiting examples of such VOCs may include acetaldehyde, acetic acid, acetone, acetonitrile, acrolein, acrylamide, acrylonitrile, allyl alcohol, allyl chloride, aminoethanol, androstenone, androstadienone, aniline, benzyl chloride, butane thiol, butyl alcohol, butyl amine, chloroacetaldehyde, chlorobenzene, chloroform, cyclohexanol, dichlorobenzene, dichloromethane, dimethylamine, dihydroxymethane, dioxane, ethanethiol, ethyl acetate, ethylamine, formaldehyde, formic acid, geosmin, methyl mercaptan, methyl acetate, methyl acrylate, methyl bromide, 1-octen-3-ol, indole, skatole, methyl ethyl ketone, phenol, propylene oxide, tetrahydrofuran, vinyl chloride and derivatives thereof.

In some embodiments, the VOCs are indole and indole derivatives.

In some embodiments, the VOCs are indole and skatole.

The invention further provides a bioelectronic sensor for detecting presence of at least one indole, the sensor comprising a single carbon nanotube (CNT) covalently immobilizing a single receptor, as defined and selected, wherein association/binding/interaction of the at least one indole to said receptor allows for a measurable electric field effect.

In some embodiments, the receptor is mosquito-derived indolergic odorant receptor (OR), and the bioelectronic sensor is thus provided for detecting presence of at least one indole, the sensor comprising a single carbon nanotube (CNT) covalently immobilizing a single mosquito-derived indolergic odorant receptor (OR), wherein association/binding/interaction of the at least one indole to said receptor allows for a measurable electric field effect.

The bioelectronic sensor of the invention is a single molecule field effect transistor (smFET) which comprises a biological recognition moiety in the form of a receptor, e.g., a mosquito-derived indolergic odorant receptor, ORx (selected from OR2, OR9 and OR10), which plays a role in the selectivity of the sensor towards the VOC, e.g., indole, molecules, and a non-biological or electronic part which role is to maintain or increase sensitivity of the sensor. The two parts of the sensor are associated via a carbon nanotube (CNT) to produce the transistor device.

Thus, the invention further provides a smFET disposed on a surface of a substrate, the smFET comprising one CNT and a capture probe covalently coupled thereto, wherein the capture probe comprises at least one receptor, e.g., a mosquito-derived indolergic odorant receptor (ORx), configured to bind or associate to at least one VOC, e.g., indole, and wherein the smFET further comprises at least one electrode assembly disposed proximate opposing ends of the one CNT to electrically couple the one CNT to the substrate.

The single-molecule bioelectronics offers an experimental approach based on direct electronic transduction of specific binding into electrons. Direct electronic transduction avoids the use of optics and light sources and allows low-formfactor devices as well as delivers signal levels that are orders of magnitude higher than those achieved with optical detectors.

Single-molecule field-effect transistors (smFETS) have the unprecedented ability to reach submicrosecond time scales in a noninvasive, label-free study of biomolecular interactions and kinetics, overcoming the limitations of existing techniques.

The CNT-smFET device of the invention is characterized by a conductance that is sensitive to charges localized within a few Debye lengths of a point defect that is generated on the CNT, e.g., SWCNT, sidewall. This site of functionalization serves as the point of attachment of a CNT-tethered OR/Orco molecule under study. Under a source-drain voltage bias of 100 mV, the current signal level of a typical smFET is tens of nanoamperes (nA).

In some embodiments of a device of the invention, the receptor is Orco or OR or a combination of the two, acting as a biorecognition element used with a custom-developed bioelectronic assay platform in the form of biofunctionalized CNT-FET array that is assembled into a biochip interfacing a printed circuit board (PCB). The array is segmented into specific biosensing regions enabling multiple ligand bindings to be interrogated in real-time. The board may include several dozen or several hundred independently addressable measurement channels that are simultaneously interrogated in real-time. The drain and source potentials for each channel are fully tunable and are composed of at least one gain stage and an anti-aliasing filter topology of high order (at least second-order). An FPGA module may be incorporated to interface the hardware and software. The PCB also includes multiplexers, decoders, and analog-to-digital converters. The smFET biochip may be packaged via a chip-carrier and mounted on the board. Designated software enabling real-time measurements and data acquisition may also be used. Alternatively, CMOS integrated biochips may be used, which contain all the required electronics on-chip and can therefore include several thousand to millions smFET devices on a single chip.

A designated microfluidic flow channel may also be present, which includes inlets and outlets for the introduction of different reagents. The channel may be fabricated from a silicon elastomer such as poly-dimethylsiloxane (PDMS) or any other biocompatible polymer.

The capture probe or biorecognition element is not DNA or a nucleotide or any other type of nucleic acids. In all devices of the invention, the capture probe is a receptor, being in some embodiments an OR or a membrane enriched therewith that is immobilized by covalent association, directly or indirectly, to the CNT. Where the covalent association is indirect, namely via a linking atom or a linker moiety, the linker moiety may be selected not to substantially alter the structure and function of the immobilized biological recognition moiety and at the same time provide an irreversible binding. The linker is further selected to control the alignment of the OR so as to ensure sensitivity, high gain and sensor reproducibility. A non-limiting example of such a linker is an amine-modified phospholipid that is conjugated to the CNT defect site via the amine group while the lipid tails are protruding in the bulk. These lipid tails can therefore functionally align the OR- or Orco- or Orco-OR-containing membrane fragment (or any other artificial membrane) through hydrophobic interactions of the protruding lipid tails and membrane bilayer.

The linker moiety is associated to the CNT via a single carbon atom on the CNT backbone (through a point defect on a portion of the CNT generated by either physicallyconfined or electrochemically-controlled reduction of diazonium compounds or any other organic compound which is a small molecule of a molecular weight below 1 kDa). In some embodiments, the linker moiety is a chain-like molecule structured in a continuous chain, which is optionally selected from peptides, phospholipids, polymers, conductive polymers, hydrophobic polymers, hydrophilic polymers and others.

In an exemplary smFET according to the invention, the sensor is configured as a carbon nanotube device disposed on a substrate, which can be a silicon substrate and can have a silicon oxide layer disposed thereon. The capture probe is immobilized onto the CNT and can be coupled to a source electrode and a drain electrode, each of which being disposed at opposing ends of the CNT. To form source and drain electrodes a metal, such as titanium, can be deposited onto the substrate. The source and drain electrodes can be passivated with a photoresist or an e-beam resist. The smFET can be configured to detect indole binding at a relatively high signal-to-noise ratio.

Upon interaction with the VOC, e.g., indole, molecule various changes can occur that can result in an altered charge distribution near the CNT. In one case, a conformational change in the biological recognition moiety takes place, resulting in an altered charge distribution near the CNT, which in turn affects local electric field and a modulated conductance of the CNT. This change in the electric field may be measured and quantified.

As noted herein, in some embodiments, the biological recognition moiety is a mosquito-derived indolergic odorant receptor (OR). The OR receptor (a peptide) may be derived from any mosquito species. In some embodiments, the mosquito species is derived from the mosquito genus Aedeomyia, *Aedes*, *Anopheles*, Armigeres, Ayurakitia, Borachinda, Coquillettidia, *Culex*, *Culiseta*, Deinocerites, Eretmapodites, Ficalbia, Galindomyia, Haemagogus, Heizmannia, Hodgesia, Isostomyia, Johnbelkinia, Kimia, Limatus, Lutzia, Malaya, *Mansonia*, Maorigoeldia, Mimomyia, Onirion, Opifex, Orthopodomyia, *Psorophora*, Runchomyia, Sabethes, Shannoniana, Topomyia, Toxorhynchites, Trichoprosopon, Tripteroides, Udaya, Uranotaenia, Verrallina and/or Wyeomyia.

In some embodiments, the mosquito genus is *Aedes*.

In some embodiments, the mosquito is selected from *Aedes australis, Aedes aboriginis, Aedes aegypti, Aedes africanus, Aedes albolineatus, Aedes alboniveus, Aedes albopictus, Aedes albolineatus, Aedes alboscutellatus, Aedes aloponotum, Aedes amesii, Aedes annulipes, Aedes arboricola, Aedes argenteoventralis, Aedes atlanticus, Aedes atropalpus, Aedes aurifer, Aedes aurimargo, Aedes aurotaeniatus, Aedes axitiosus, Aedes bahamensis, Aedes barraudi, Aedes bekkui, Aedes bicristatus, Aedes bimaculatus, Aedes brelandi, Aedes brevitibia, Aedes burger, Aedes cacozelus, Aedes camptorhynchus, Aedes canadensis, Aedes cantans, Aedes cantator, Aedes caspius, Aedes cataphylla, Aedes cavaticus, Aedes cinereus, Aedes clivis, Aedes communis, Aedes cordellieri, Aedes coulangesi, Aedes cretinus, Aedes dasyorrhus, Aedes deserticola, Aedes desmotes, Aedes domesticus, Aedes dupreei, Aedes eldridgei, Aedes epactius, Aedes esoensis, Aedes fulvus, Aedes furcifer, Aedes futunae, Aedes* Ganapathi, *Aedes geminus, Aedes gombakensis, Aedes grassei, Aedes grossbecki, Aedes harinasutai, Aedes helenae, Aedes hensilli, Aedes hesperonotius, Aedes hoogstraali, Aedes horotoi, Aedes imprimens, Aedes inermis, Aedes infirmatus, Aedes intrudens, Aedes japonicus, Aedes kochi, Aedes kompi, Aedes koreicus, Aedes lineatopennis, Aedes luteocephalus, Aedes madagascarensis, Aedes*

*malayensis, Aedes marshallii, Aedes masculinus, Aedes mediolineatus, Aedes mediovittatus, Aedes mefouensis, Aedes melanimon, Aedes meronephada, Aedes michaelikati, Aedes mitchellae, Aedes mohani, Aedes monticola, Aedes muelleri, Aedes nevadensis, Aedes ngong, Aedes niphadopsis, Aedes niveus, Aedes notoscriptus, Aedes nummatus, Aedes ostentation, Aedes palpalis, Aedes pembaensis, Aedes pexus, Aedes polynesiensis, Aedes pseudoniveus, Aedes pseudonummatus, Aedes pulchritarsis, Aedes pullatus, Aedes pulverulentus, Aedes punctodes, Aedes punctor, Aedes purpureipes, Aedes purpureifemur, Aedes rempeli, Aedes rusticus, Aedes scapularis, Aedes schizopinax, Aedes scutellaris, Aedes sollicitans, Aedes spilotus, Aedes squamiger, Aedes stricklandi, Aedes sylvaticus, Aedes taeniorhynchus, Aedes taylori, Aedes thelcter, Aedes thibaulti, Aedes thomsoni, Aedes tiptoni, Aedes togoi, Aedes tormentor, Aedes tortilis, Aedes turneri, Aedes varipalpus, Aedes ventrovittis, Aedes vexans, Aedes vigilax, Aedes vittatus, Aedes washinoi, Aedes* wauensis and *Aedes* zoosophus.

In some embodiments, the mosquito-derived indolergic receptor is derived from *Aedes aegypti.*

In some embodiments, the receptor is a mammalian androstenone receptor.

In some embodiments, the receptor is a fly geosmin receptor.

In some embodiments, the biological recognition moiety is a mosquito-derived indolergic receptor OR2, OR9 or OR10. In some embodiments, the receptor is OR9.

In some embodiments, the biological recognition moiety is a mosquito-derived indolergic receptor OR8.

In some embodiments, the OR9 is derived from the genus *Culex* and *Aedes*, e.g., *Aedes aegypti* and *Aedes albopictus.*

In some embodiments, the mosquito-derived indolergic receptor is an OR9 homolog derived from the mosquito subfamily Culicinae.

In some embodiments, the mosquito-derived indolergic odorant receptor derived from *Aedes aegypti* is selected amongst such having a GenBank number OR2: ACH69138, OR9: ACH69140 and/or OR10: ACH69137.

Other mosquito-derived indolergic receptors include OR2, OR9 and OR10 homologs such as AEX65778, ADF42901, KFB39839, ACH69144, XP_310173, AIO10776, ACH69149, ETN60992, m. 10291, KXJ75419, XP_001864543, KXJ77288, ADF42902, ACH69146, XP_310172, ACH69150, KFB39838, ETN65485, m.26775.

Other mosquito-derived 1-octen-3-ol receptors include OR8 homologs such as NP_001345386, DAA80358, XP_029725568, ALV83717, XP_001864496, KFB40732, XP_321153, m.134618.

Fly-derived geosmin receptors include OR56a homologs such as NP_523796, XP_001361440, ABL73972, ALC42765.

Mammalian-derived steroid receptors include OR7D4 homologs and variants such as NP_001005191, NP_001161837, ACZ52483, XP_002828654, NP_001266172, ACZ52482, EHH59162, XP_011849674, NP_001161801, NP_001295931, ACZ52479, XP_011810305.

In some embodiments, the biological recognition moiety is OR-co-receptor (Orco). In cases where Orco is used, interaction with the indole induces an opening of a cation ion channel and a subsequent cation influx transiently locating positive charges near the CNT, thereby resulting in a significant electric field-effect.

The CNT may be selected amongst any of the known carbon nanotube systems. The term includes single-walled carbon nanotube (swCNT), double-walled carbon nanotube (dwCNT), multi-walled carbon nanotube (dwCNT) and others. In some embodiments, the CNT is swCNT.

In some embodiments, in a device of the invention a single OR9 receptor or Orco is covalently associated to a single swCNT molecule.

Various aspects of chemo-electronic transduction of binding events using OR or Orco agonists may be utilized for monitoring the device conductance in real-time. The binding affinities of OR or Orco ligands are generally low and will enable the monitoring of capture and release dynamics. In addition, the application of electric potential by a gate electrode has an effect on the receptor conformational behavior and binding activity thus allowing the further study of the thermodynamic properties of the OR-indole system.

In some implementations of a device of the invention, the bioelectronic sensor of the invention is provided in the form of isolated OR- or Orco-functionalized CNT-FET arrays assembled as a biochip interfacing a printed circuit board (PCB). The array may be segmented into specific biosensing regions enabling multiple indole binding to be interrogated in real-time. The PCB contains all electronic components required for signal acquisition, such as amplifiers, analog-to-digital and digital-to-analog converters, multiplexer, and others.

The combination of CNT-smFET and ORs has broader clinical diagnostic implications. The search for non-invasive disease biomarkers has yielded a wide range of biomarkers of lung cancer, IBD and diabetes as well as biomarkers of infectious diseases. The extensive sequence diversity of ORx suggests they may be used to identify biomarkers either by natural recognition, cross-reactivity or, as a result of targeted evolution. Employing ORx in the detection of biomarkers has a huge potential in point-of-care diagnostics.

In addition, this invention enables high throughput VOC screening, relevant for environmental monitoring, screening of non-hazardous mosquito repellents, identification of semiochemicals, etc. Prevention of vector-borne infectious diseases is largely based on vector control, specifically mosquitoes. New tools and technologies are constantly being pursued to reduce disease spread. Among the different approaches, the development of non-hazardous repellents/attractants stands in the frontline. Thus, tools that affordably provide fast and accurate reports of drug-dependent receptor activation or structural rearrangement and enable screening of large libraries of compounds are urgently required. The bioelectronic experimental system described herein simultaneously fulfill both of these requirements.

The fabrication methodology presented may alleviate the limitations of CNT-FET manufacturability. In the microelectronics industry mass scaling of CNT devices is still hampered by low manufacturability. While the fabrication of microprocessors indeed requires maximal uniformity across devices the production requirements of CNT-smFET bioelectronic sensors are less stringent. As opposed to microprocessors, CNT-smFET sensors encodes information temporally and signal amplitudes can vary as long as there is sufficient signal-to-noise ratio (SNR) contrast between the conductance states of the system. Consequently, CNT to CNT variability does not necessarily compromise manufacturability.

A sensor of the invention is selective and sensitive towards indoles. As noted above, the advantage of indole ORs, as opposed to pheromone receptors, is their selective and sometime specific relationship to indole and skatole and other indole derivatives. Indole and skatole, along with volatile sulfur compounds are major components of breath odor and halitosis and may be used as clinical markers for the diagnosis of halitosis and underlying etiologies, including metabolic diseases and oral inflammations. Patients with bowel cancer have higher fecal skatole content than healthy individuals suggesting that skatole may be a valuable biomedical marker in this context as well. Thus sensors of the invention may be used for detecting or sensing the presence of a variety of indoles, which may be the products of biological processes indicative of a disease or a disorder, or products of a biological or chemical degradation processes, or contamination by indole compounds and others. These indole compounds may be any compound or material comprising an indole structure that is a substituted indole, a ring-fused indole or any indole analog e.g., indole (1H-indole), skatole, indole-3-butyric acid, indole-3-acetic acid, indole-,3-carbinol, tryptophan, beta carboline, and various indole alkaloids.

The invention further provides a method for detecting or sensing presence of at least one volatile organic compound (VOC), such as an indole, present in a sample, e.g., an air or liquid sample, the method comprising contacting a bioelectronic sensor comprising a single carbon nanotube (CNT) covalently immobilizing a single receptor optionally being a mammalian or an insect receptor, under conditions permitting association of the VOC to said receptor, wherein association of the VOC to said receptor causes a measurable electric field effect.

In some embodiments, the receptor is mosquito-derived indolergic odorant receptor (OR).

In some embodiments, the sensor is for detecting presence of at least one indole, the sensor comprising a single carbon nanotube (CNT) covalently immobilizing a single mosquito-derived indolergic odorant receptor (OR), wherein association of the at least one indole to said receptor allows for a measurable electric field effect.

In some embodiments, the OR is selected from OR2, OR9, OR10, OR co-receptor (Orco) or a combination thereof. In some embodiments, the OR is OR8.

In some embodiments, the OR is OR9 or OR9 co-receptor.

In some embodiments, the CNT is selected from single-walled carbon nanotube (swCNT), double-walled carbon nanotube (dwCNT) and multi-walled carbon nanotube (dwCNT). In some embodiments, the CNT is swCNT.

In some embodiments, the receptor is a single OR9 receptor or Orco is covalently associated to a single swCNT molecule.

In some embodiments, the sensor is a single-molecule field-effect transistor (smFET) device comprising one CNT and a capture probe covalently coupled thereto, wherein the capture probe comprises at least one receptor configured to bind or associate to at least one VOC, wherein the smFET further comprises at least one electrode assembly disposed proximate opposing ends of the one CNT to electrically couple the one CNT to a substrate onto which the smFET is disposed, wherein the capture probe is not DNA or a nucleotide.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 provides an illustration of an Orco-CNT FET. An amine-terminated lipid is covalently coupled to defects generated on a single-walled carbon nanotube (SWCNT)

sidewall via diazonium chemistry. This lipid serves as a nucleation point for the assembly of Orco-containing membrane fragment. The CNT acts as the channel in a field-effect transistor, transducing biomolecular charge into a conductance change in the FET. Binding and dissociation of targets generate random telegraph signals (RTS, shown in inset), which correspond to open and closed states of the ion channel.

FIGS. 2A-B depict CNT-FET design and fabrication. FIG. 2A-Representative illustration of metal source-drain electrode pattern, with individual CNTs bridging each pair. Also shown (right) is a microscopy image of a fabricated chip. FIG. 2B—an example of CNT-FET process flow. (a) CNTs are either CVD-grown or spun. (b) Lithography patterning for source and drain electrical contacts (e.g., Titanium). (c) Metal (e.g., titanium) deposition and photoresist removal. (d) Patterning for pseudo-reference (e.g., platinum) gate electrodes followed by (e) deposition and photoresist removal. (f) Patterning for metal (e.g., gold) bond pads.

Figure 3A:
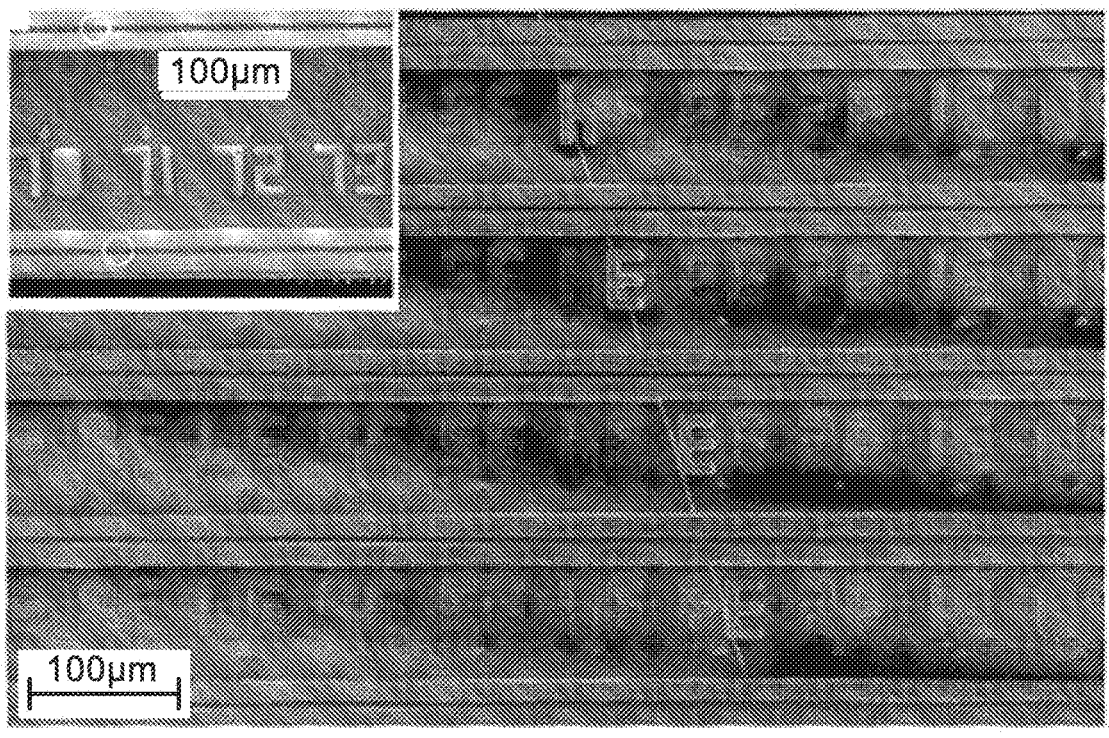
Figure 3B:
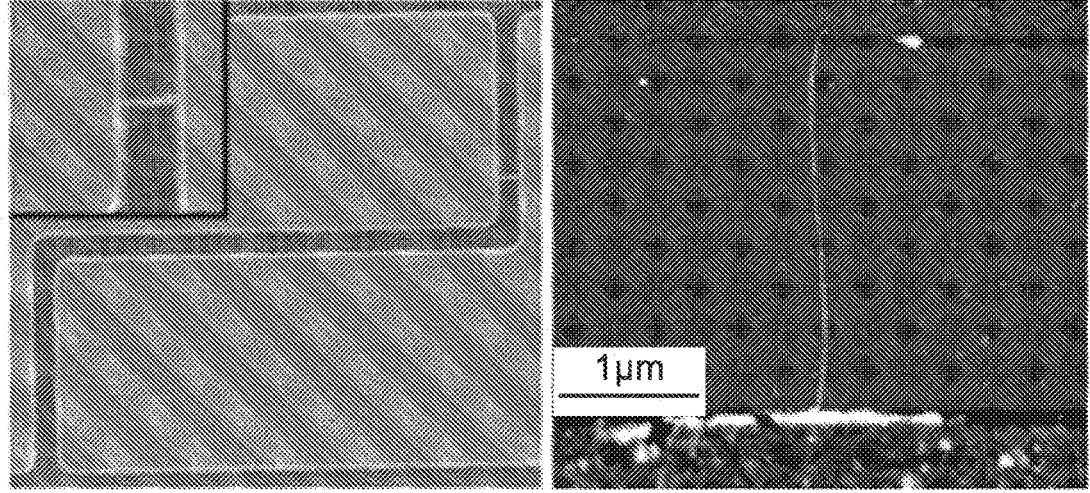
Figure 3C:
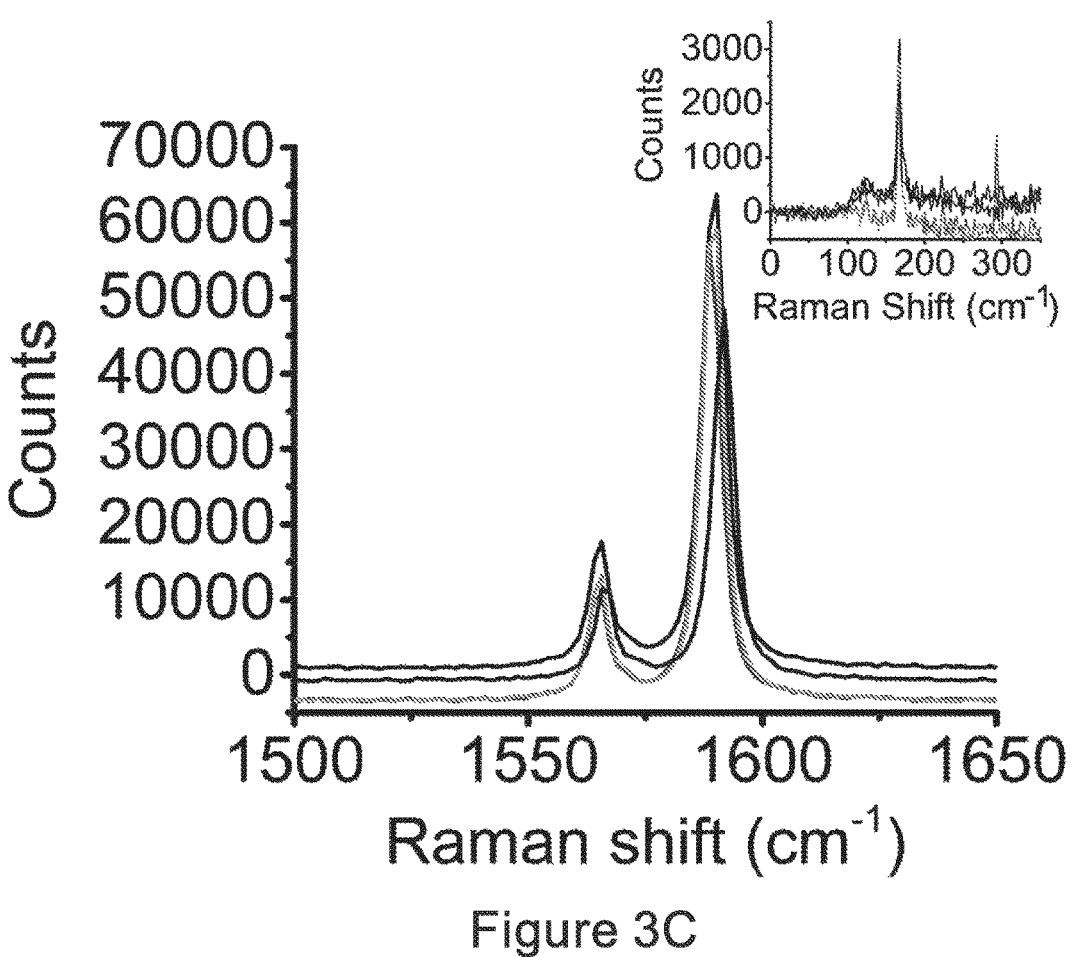
Figure 3D:
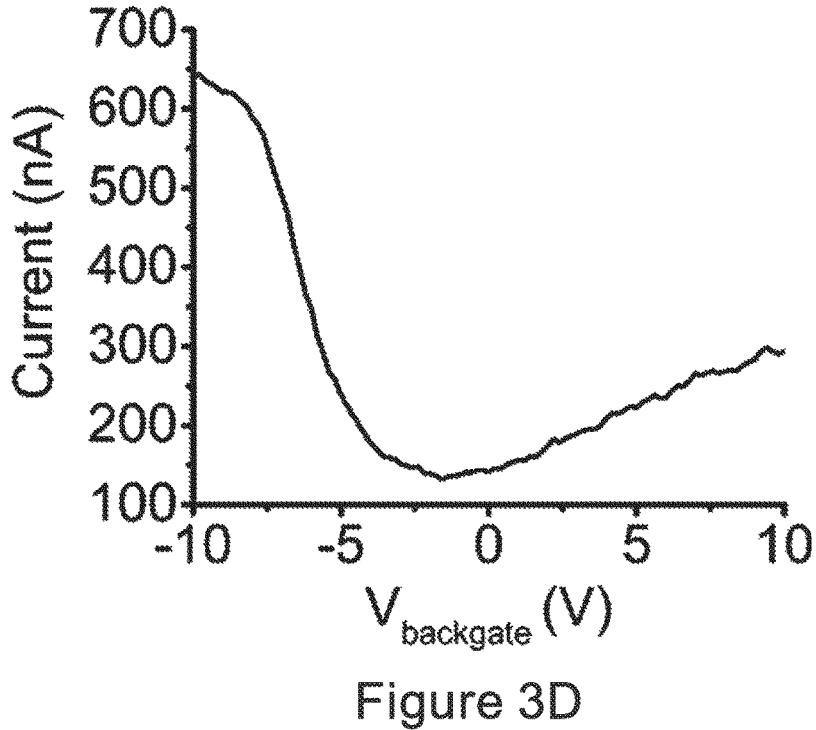

FIGS. 3A-D provide CNT FET devices characterization. FIG. 3A-SEM image showing a CVD-grown CNT spanning five electrode pairs. Inset: two isolated CNT fragments. FIG. 3B-left: spin-cast CNTs produce single-nanotube crossings. Inset: a zoomed-in of the crossing. Right: AFM image of a CNT fragment capped by a source and drain Titanium electrodes. FIG. 3C-Raman spectra collected from individual CNT fragments demonstrating reproducible Raman features, with $\omega G^+$ and $\omega G$ located at 1588 cm$^{-1}$ and 1566 cm$^{-1}$, respectively. Inset shows the RBM spectra of the same nanotubes, located at 170 cm$^{-1}$ corresponding to a diameter of 1.45 nm FIG. 3D-I-V curve of a CNT device backgated in air showing ambipolar transport characteristics.

Figure 4A:
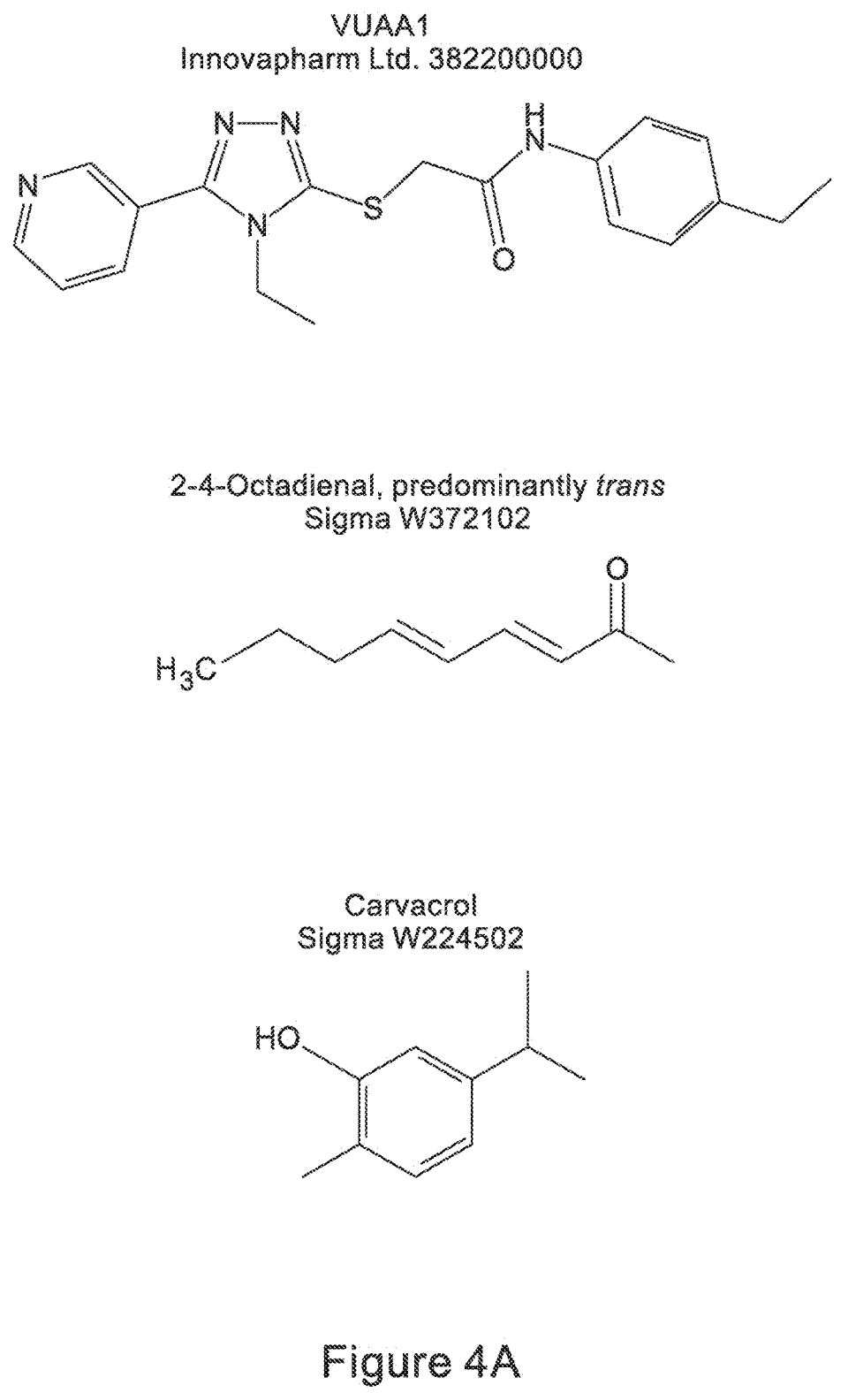
Figure 4B:
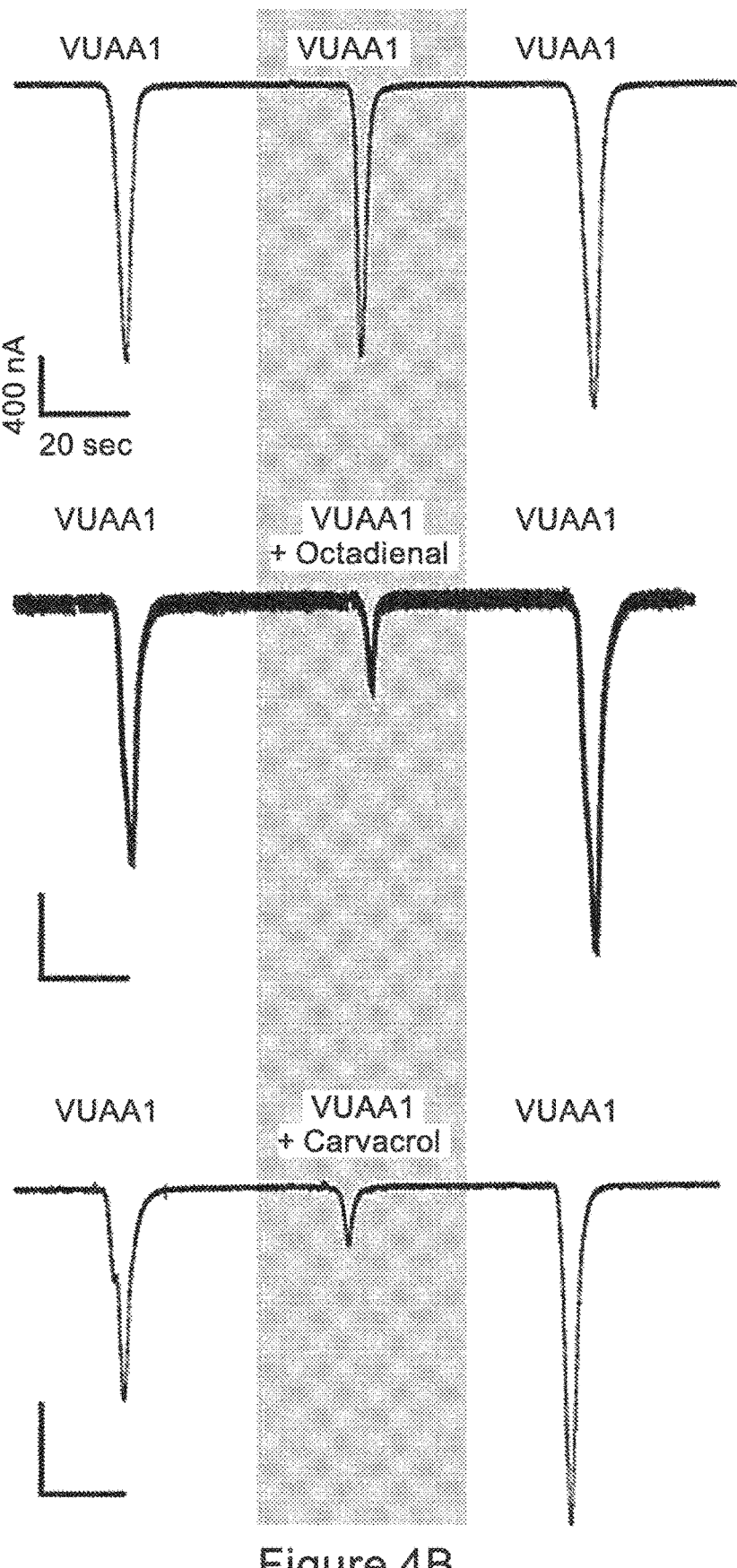
Figure 4C:
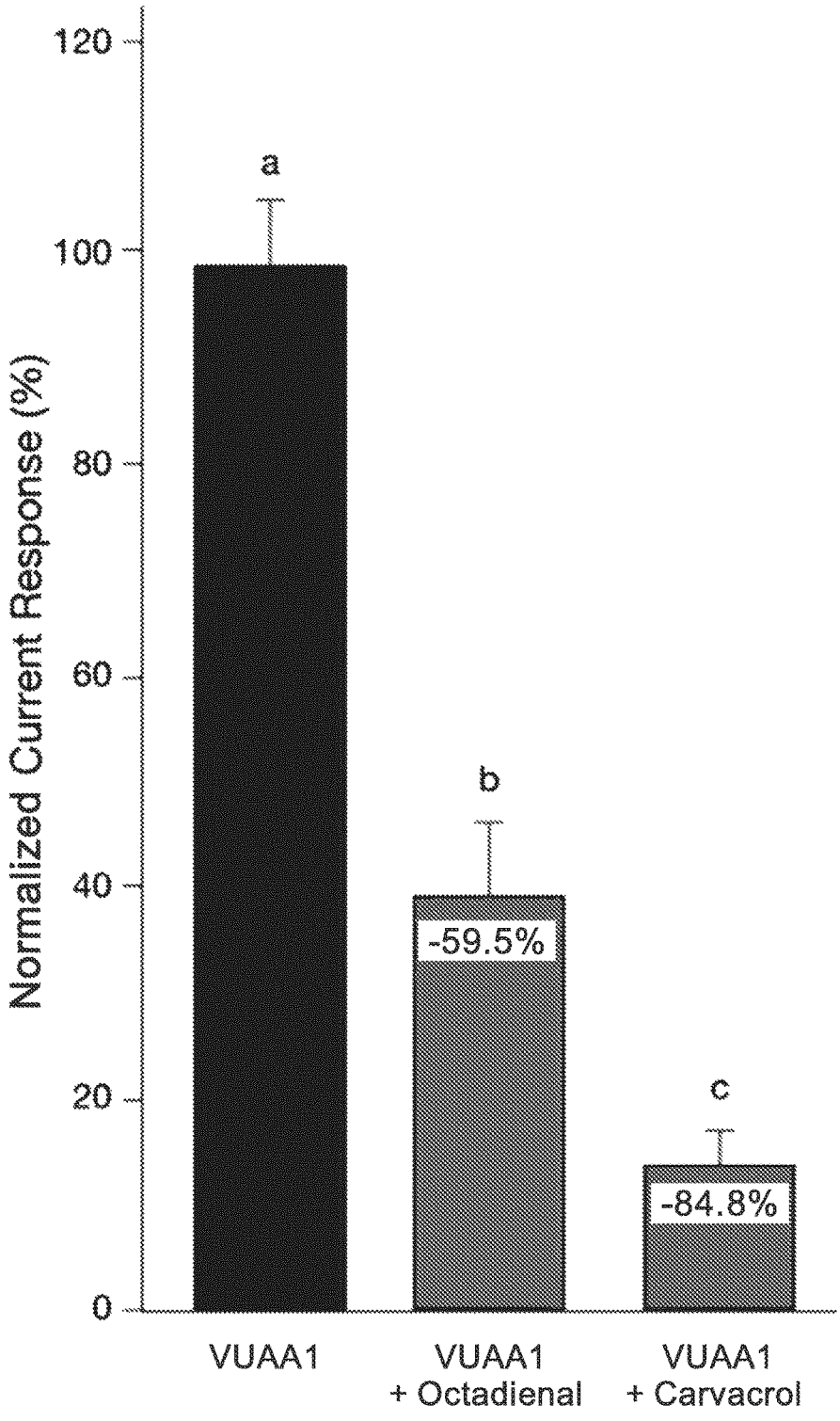

FIGS. 4A-C demonstrate how octadienal and carvacrol inhibit VUAA1-activated Orco. FIG. 4A-Chemical structures of tested compounds. FIG. 4B-Representative current traces of oocytes expressing *Aedes aegypti* Orco following exposure to 2.10-4 M VUAA1 alone or in combination with equimolar concentrations of the antagonists octadienal and carvacrol. FIG. 4C-Normalized responses of AaegOrco to VUAA1 alone or in combination with octadienal or carvacrol. Odorants effects were statistically significant (one-way ANOVA followed by Tukey's post-test; P<0.0001; mean responses+s.e.m.; VUAA1 alone, n=7; octadienal & carvacrol n=6).

Figure 5A:
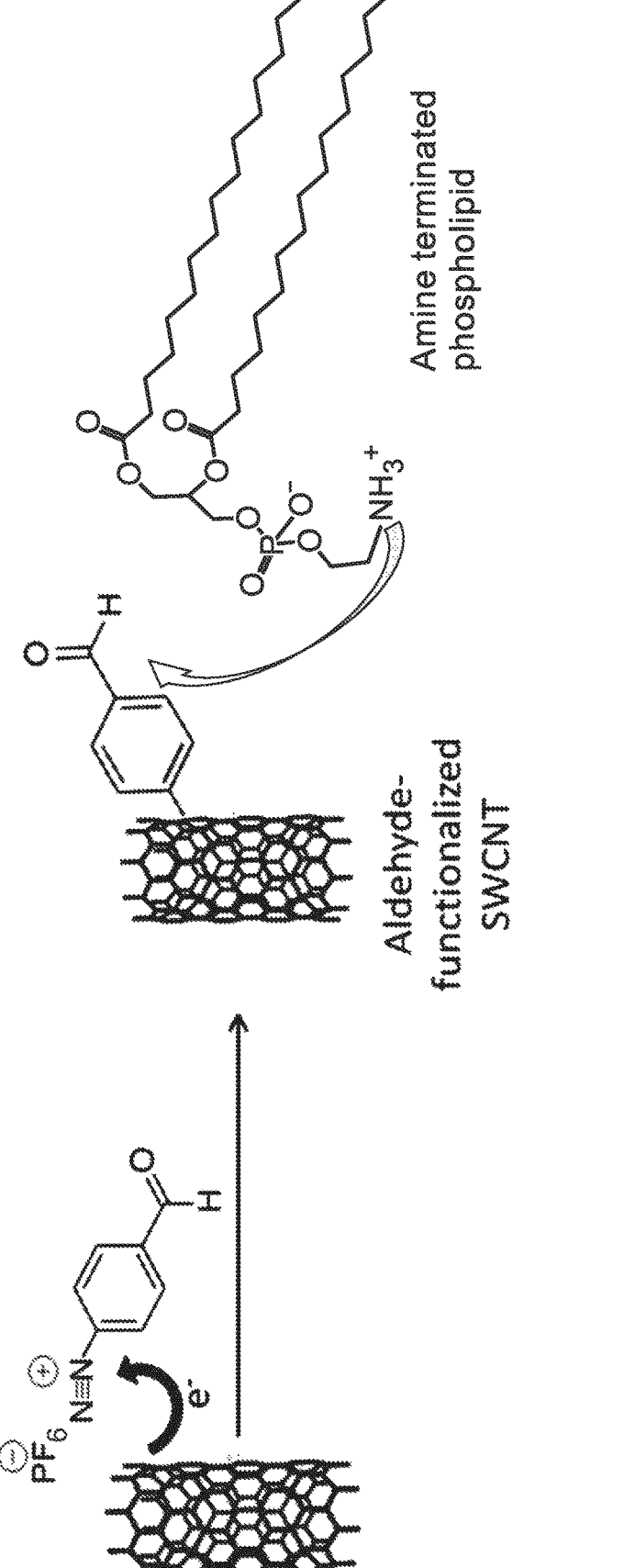
Figure 5B:
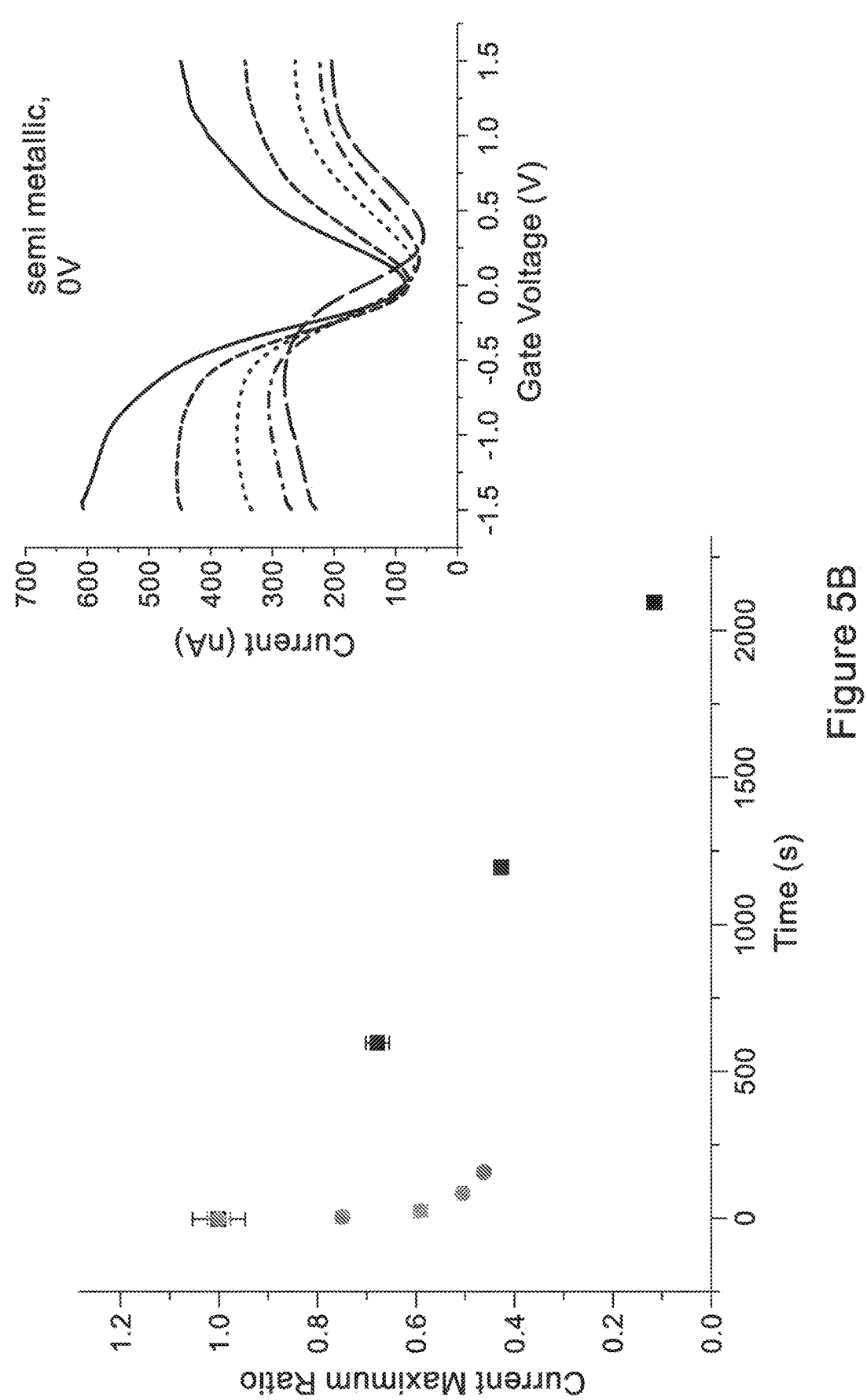
Figure 5B:
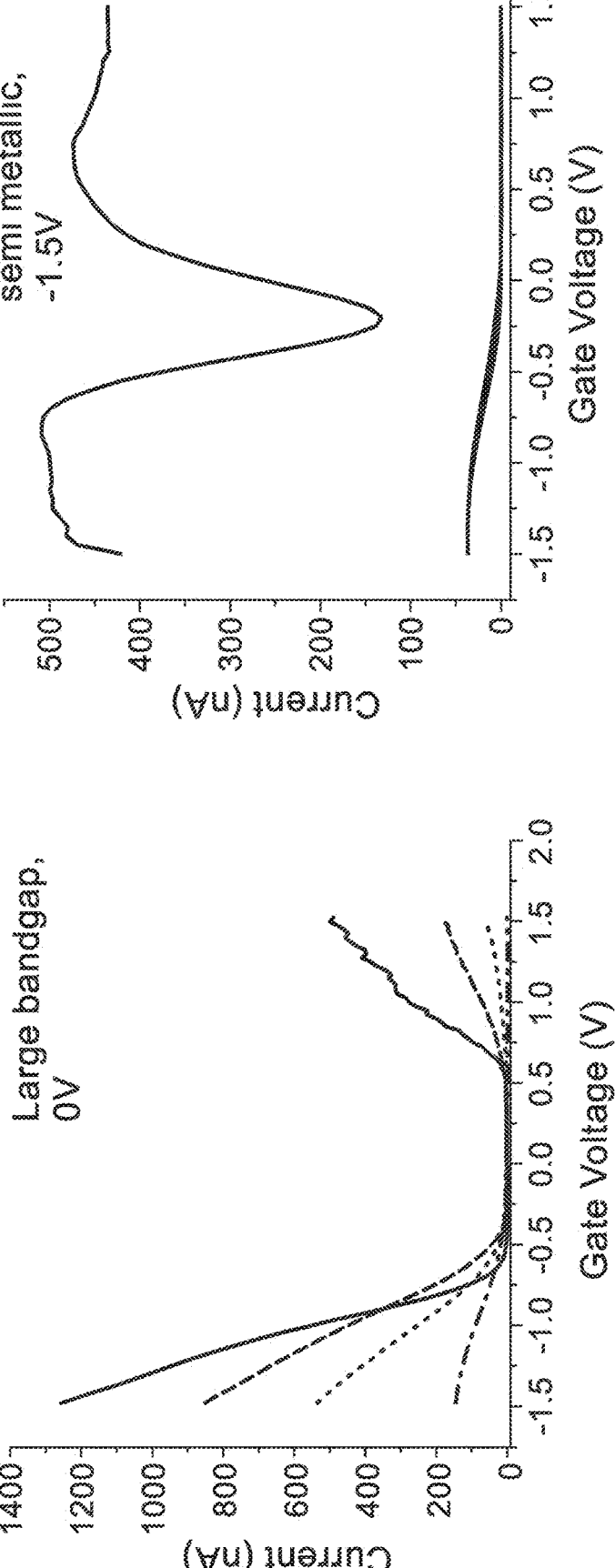
Figure 5C:
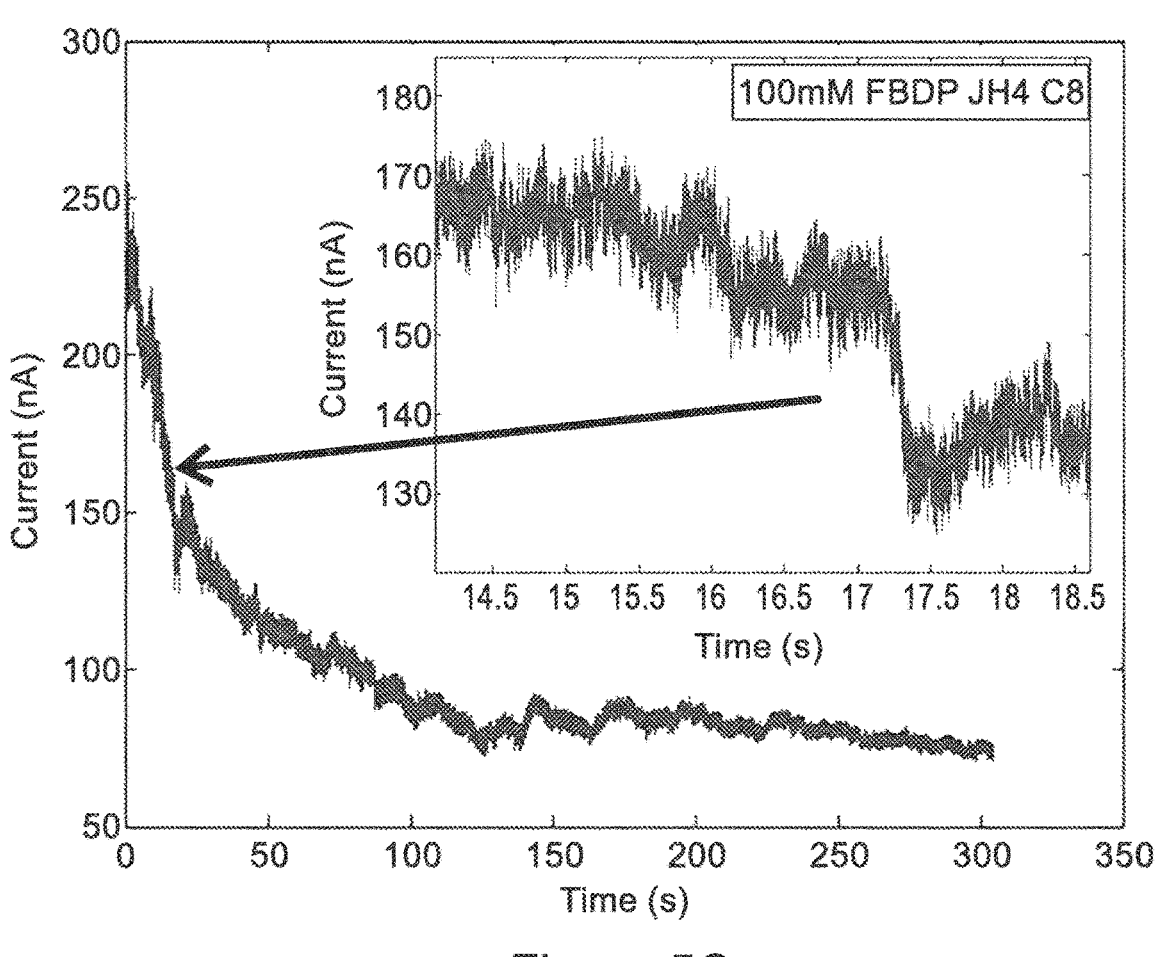
Figure 5D:
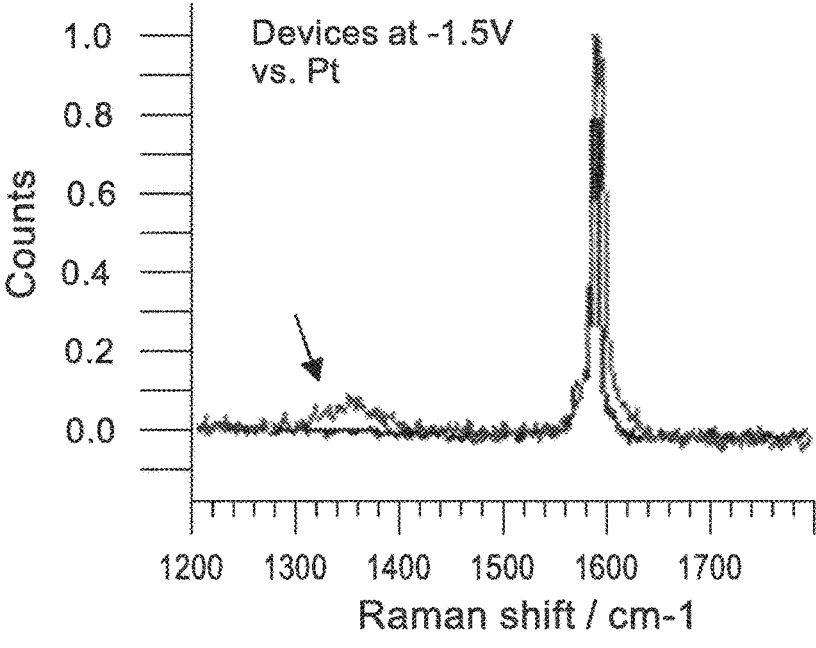
Figure 5E:
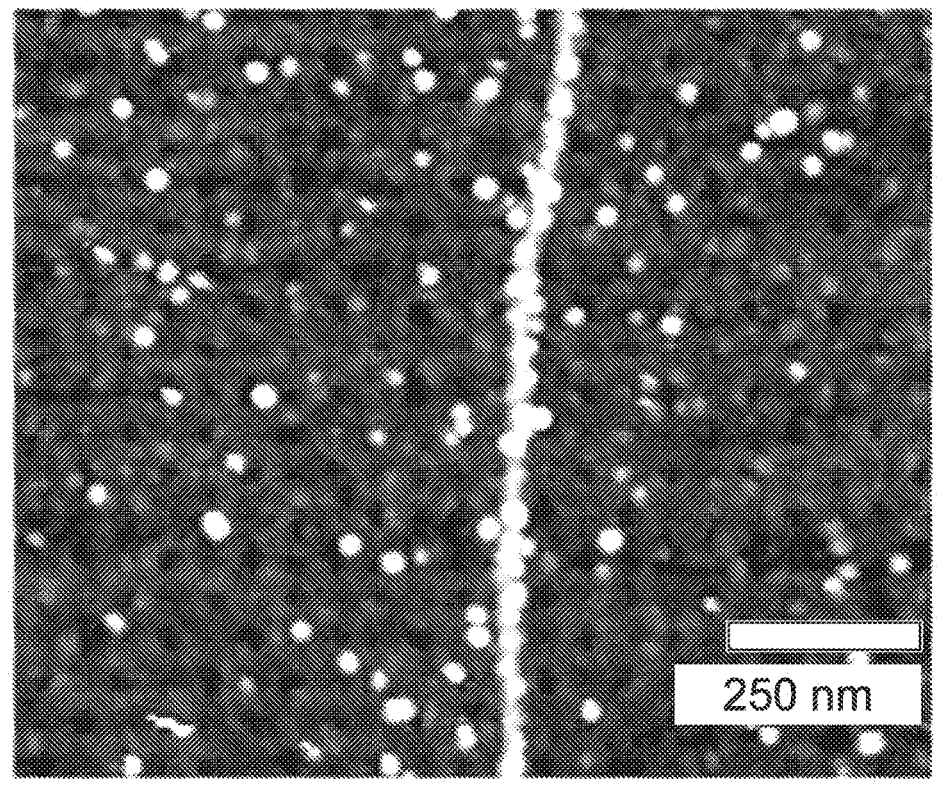

FIGS. 5A-E show electrochemically regulated functionalization of CNT FET. FIG. 5A-Complete biofunctionalization scheme includes the voltage bias induced diazonium (FBDP) reaction followed by conjugation of amine-terminated phospholipid (DPPE) via reductive amination. FIGS. 5B-D depict electrochemically-controlled CNT-FET diazonium modification. FIG. 5B-Electrical behavior of CNT devices before and after FBDP sequential exposures, as reflected by I-Vlg measured after each exposure. Decrease in on-state current is a result of carrier scattering due to orbital rehybridization. At 0V vs. platinum reference electrode, small-band-gap CNT (denoted 'semi metallic') show sharp exponential kinetics (circles) while large-band-gap CNT show very slow kinetics with longer saturation times (squares). At a sufficiently high overpotential of −1.5V, accelerated kinetics is observed resulting in reaction saturated following the first few seconds of exposure. Current values were normalized to the maximum value. FIG. 5C-Representative I-t trace of a device after FBDP introduction. Discrete current drops are observed. The resistance change due to the addition of a single sp$^3$ defect has been shown to reduce transconductance from h/4e$^2$ to h/2e$^2$. FIG. 5D-Raman spectra of CNT devices before and after reaction at −1.5V exhibited a decrease in G peak and appearance of a D peak. FIG. 5E-Specific CNT coupling of FBDP is indicated by labeling with amine-modified gold nanoparticles. Minimal background adsorption is observed.

Figure 6:
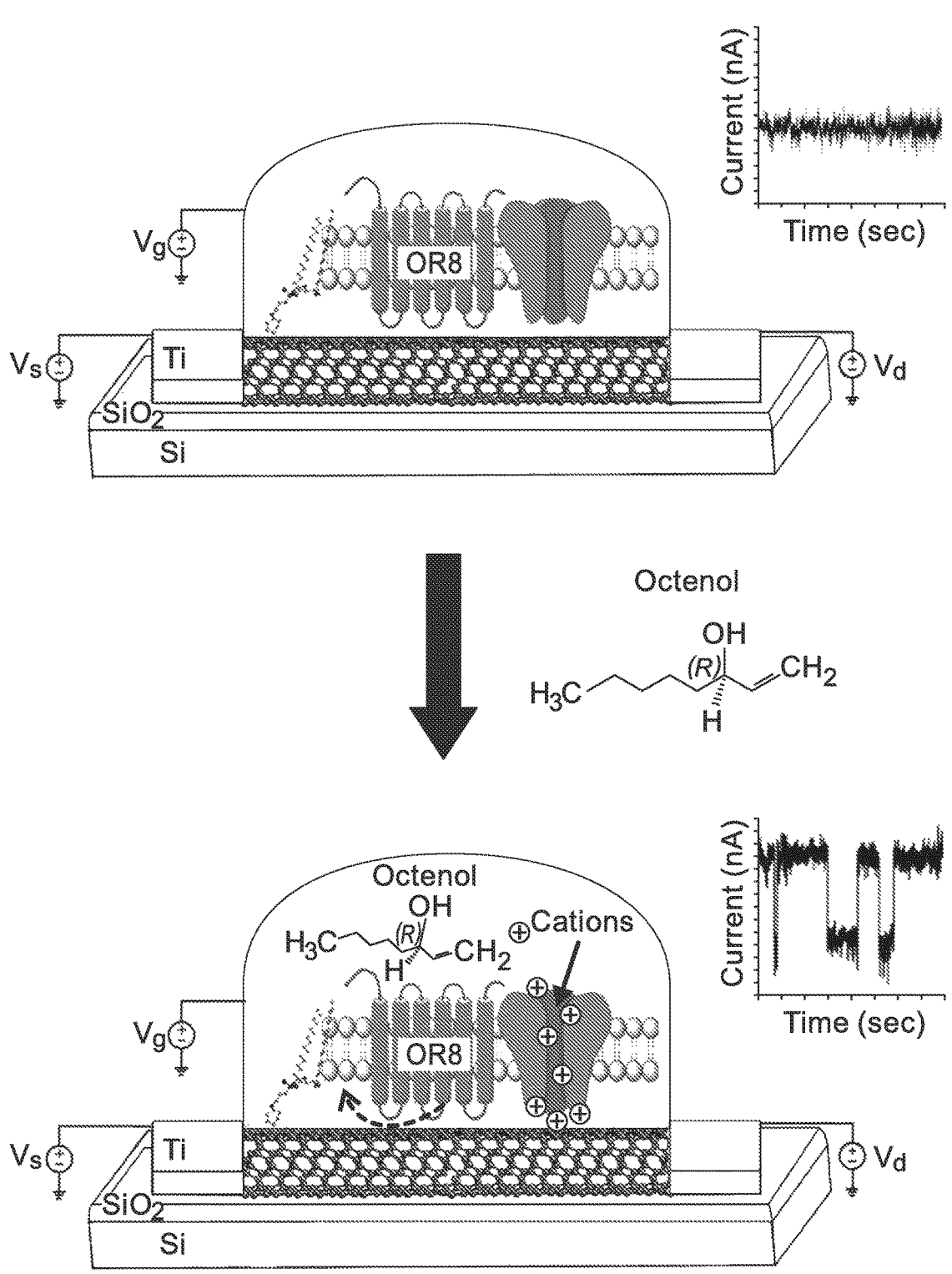

FIG. 6 illustrates an OR-CNT FET. An amine-modified lipid is covalently coupled to defects, generated on a single-walled carbon nanotube (SWCNT) sidewall via diazonium chemistry. This lipid serves as a nucleation point for the assembly of OR8-containing supported lipid bilayer (OR8 receptor is used as an example). The CNT acts as the channel in a field-effect transistor, transducing biomolecular charge into a conductance change in the FET. Binding and dissociation of targets generate random telegraph signals (RTS, shown in inset).

Figure 7A:
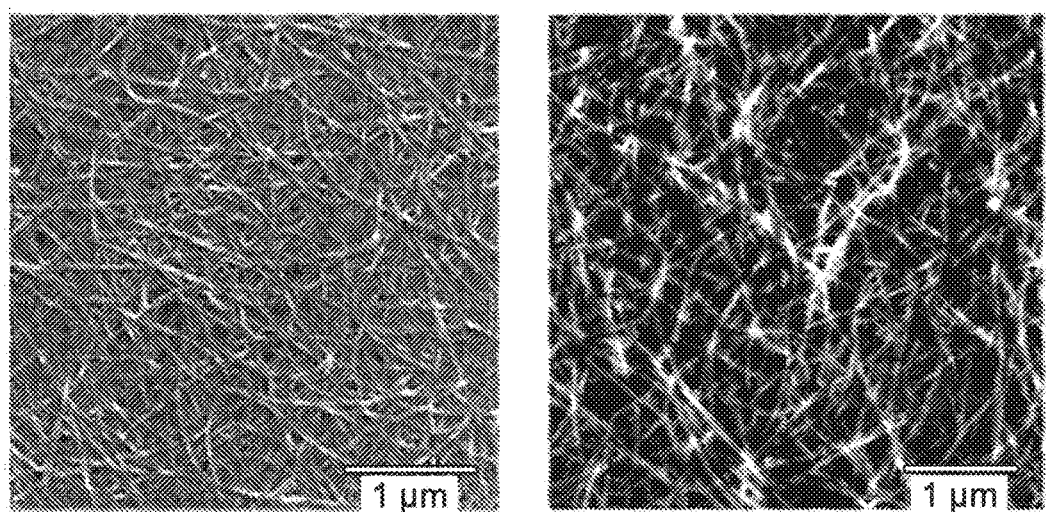
Figure 7B:
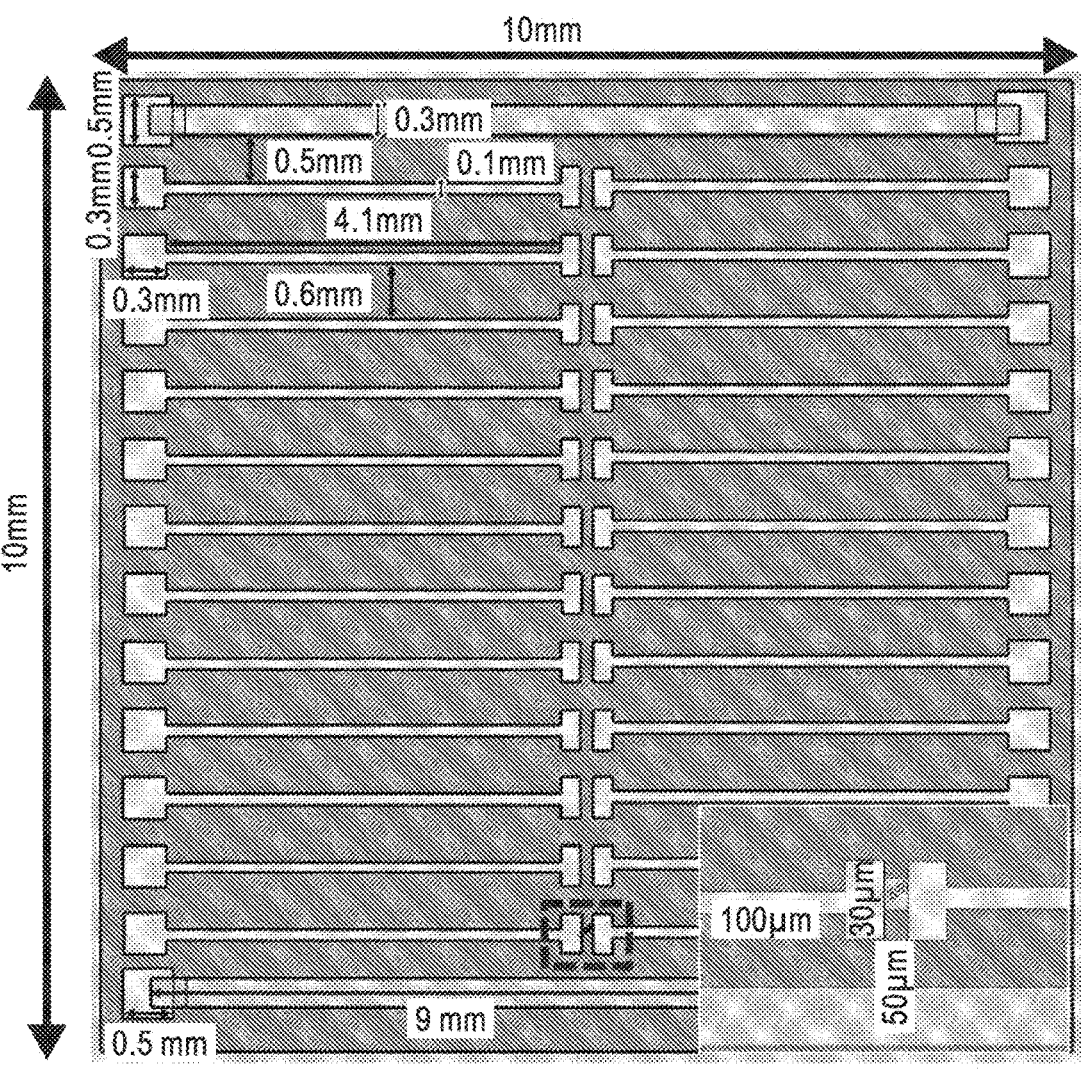
Figures 7C, 7D:
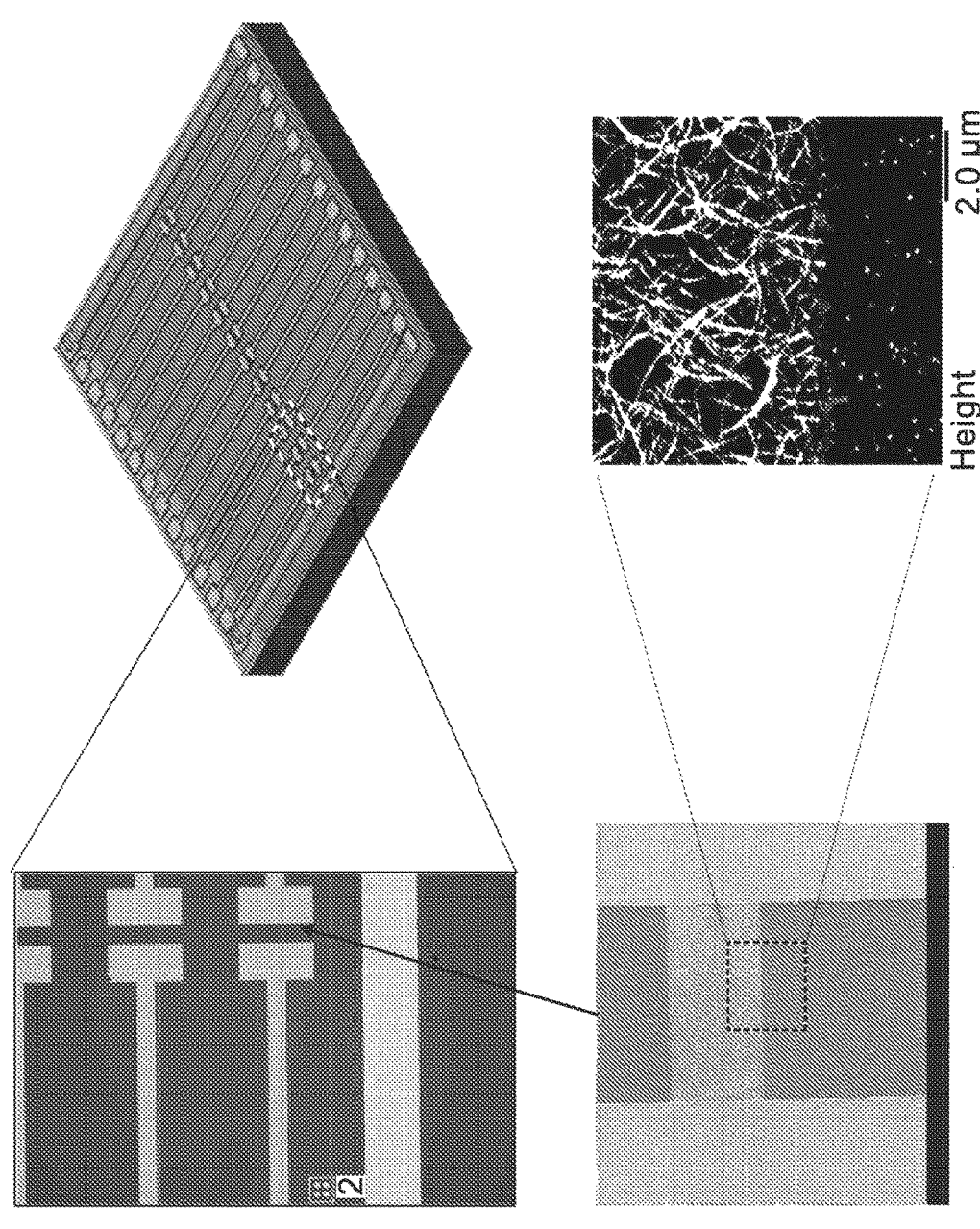

FIGS. 7A-D illustrate fabrication of OR-integrated CNT FET devices. FIG. 7A-SEM (left) and AFM (right) images showing a homogenous CNT network dispersed on a Si/SiO2 substrate. FIG. 7B-A scheme of the preliminary chip design showing an array of 12 FET devices and 2 pseudo-reference electrodes. CNT networks are patterned as a FET channel of 50 $\mu$m×100 $\mu$m (shown in inset). FIG. 7C-Platinum gate and titanium source and drain electrodes are patterned and deposited by e-beam deposition. FIG. 7D—Each CNT network device is extensively characterized structurally, using SEM and AFM, electronically by using Raman spectroscopy and finally, by measuring its I-V characteristics.

Figure 8A:
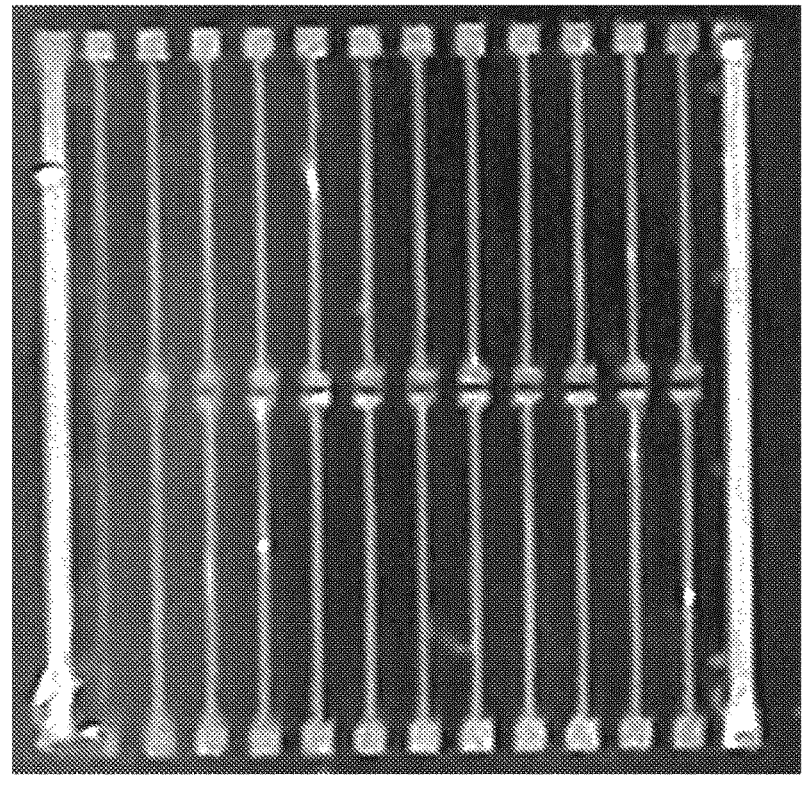
Figure 8B:
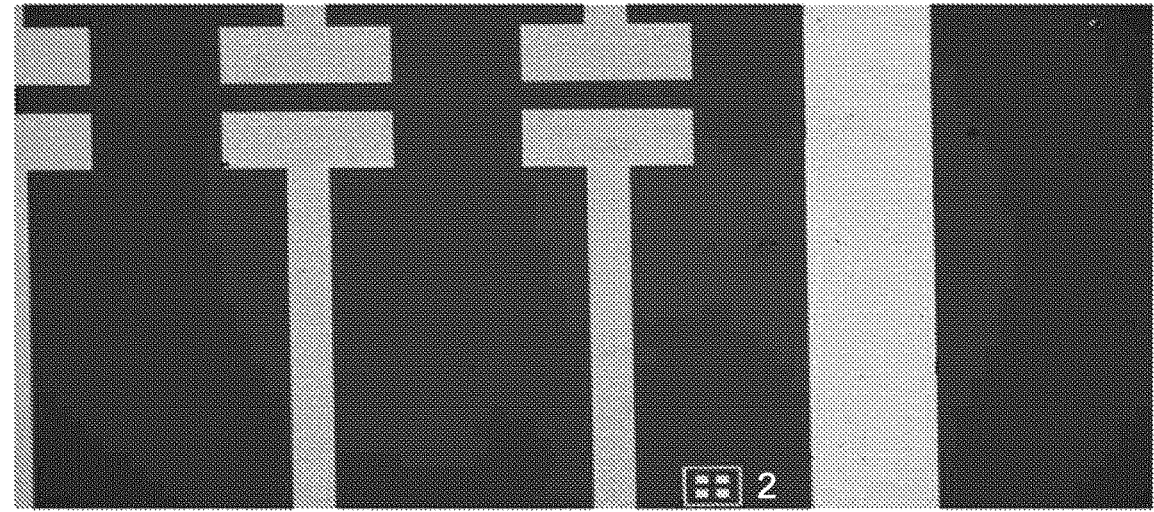
Figure 8C:
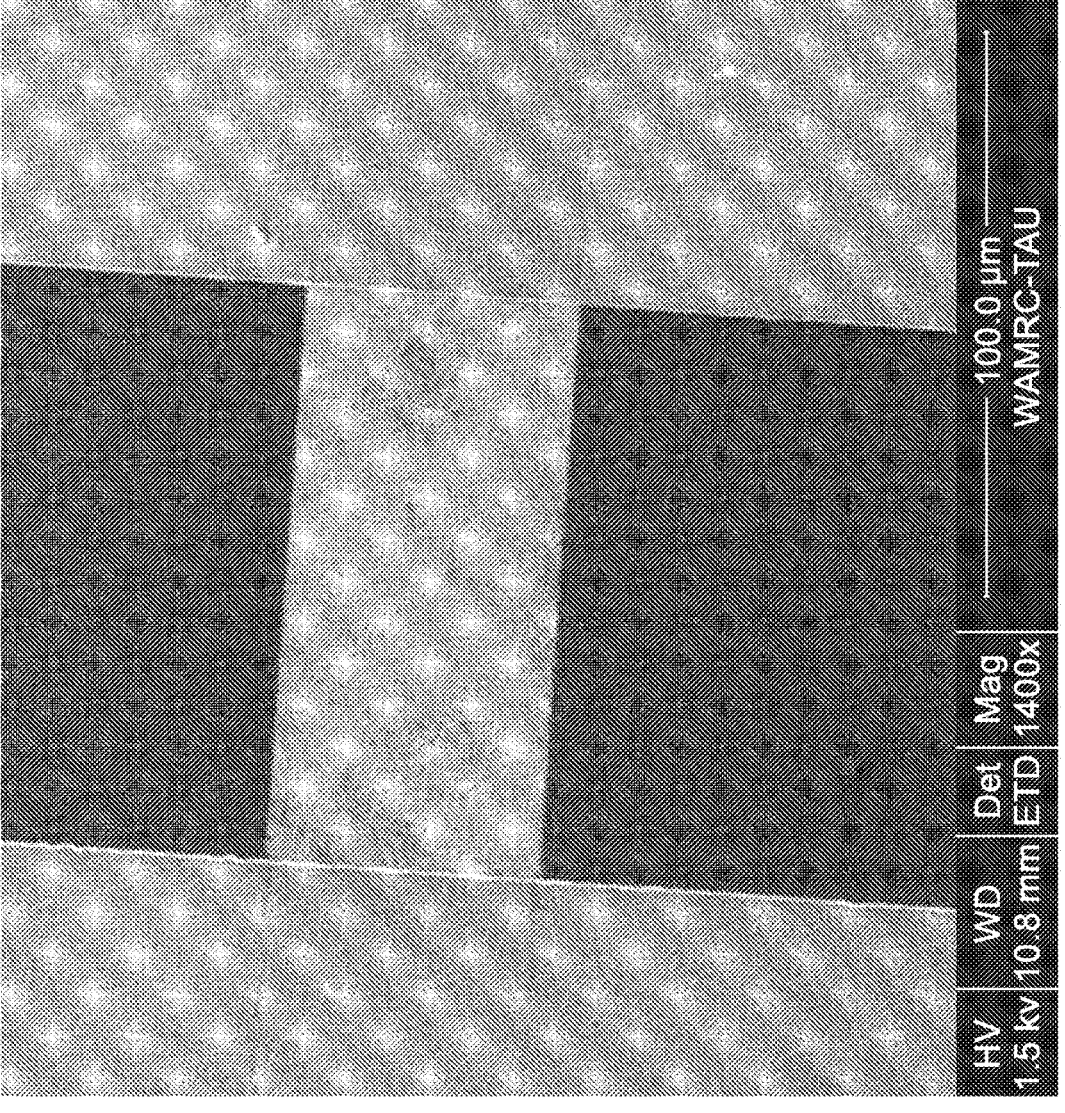

FIGS. 8A-C wherein FIG. 8A-Chip after fabrication process, FIG. 8B-Microscope image, shows gate metal and source and drain metal in magnification 5×.

FIG. 8C-SEM image of device, show the network CNT in scale bar corresponds to 100 $\mu$m.

Figures 9A, 9B:
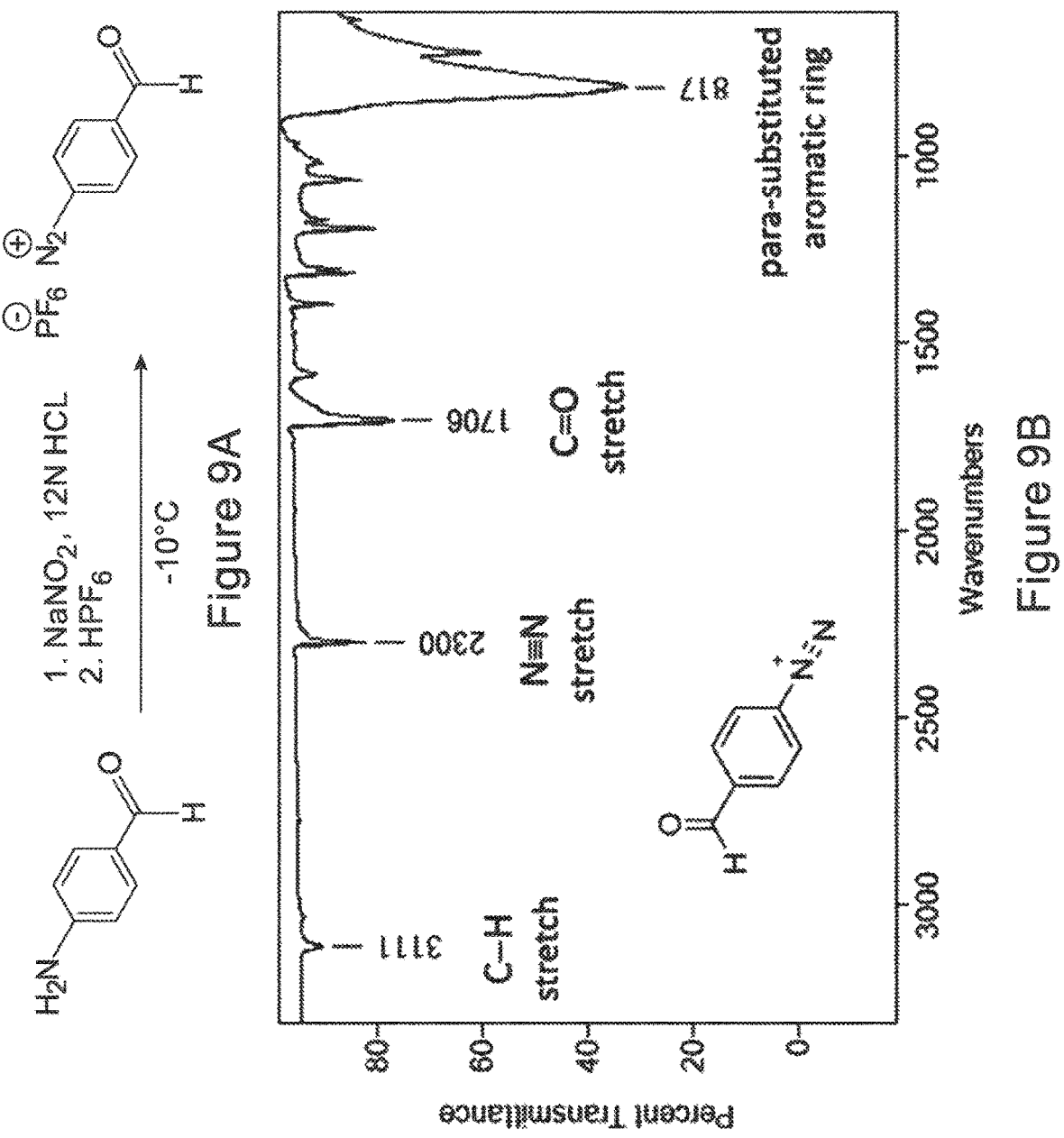

FIGS. 9A-B demonstrate FBDP synthesis and characterization. FIG. 9A-Synthesis of FBDP from 4-aminobenzaldehyde. FIG. 9B-FT-IR spectrum of the synthesized FBDP.

Figure 10A:
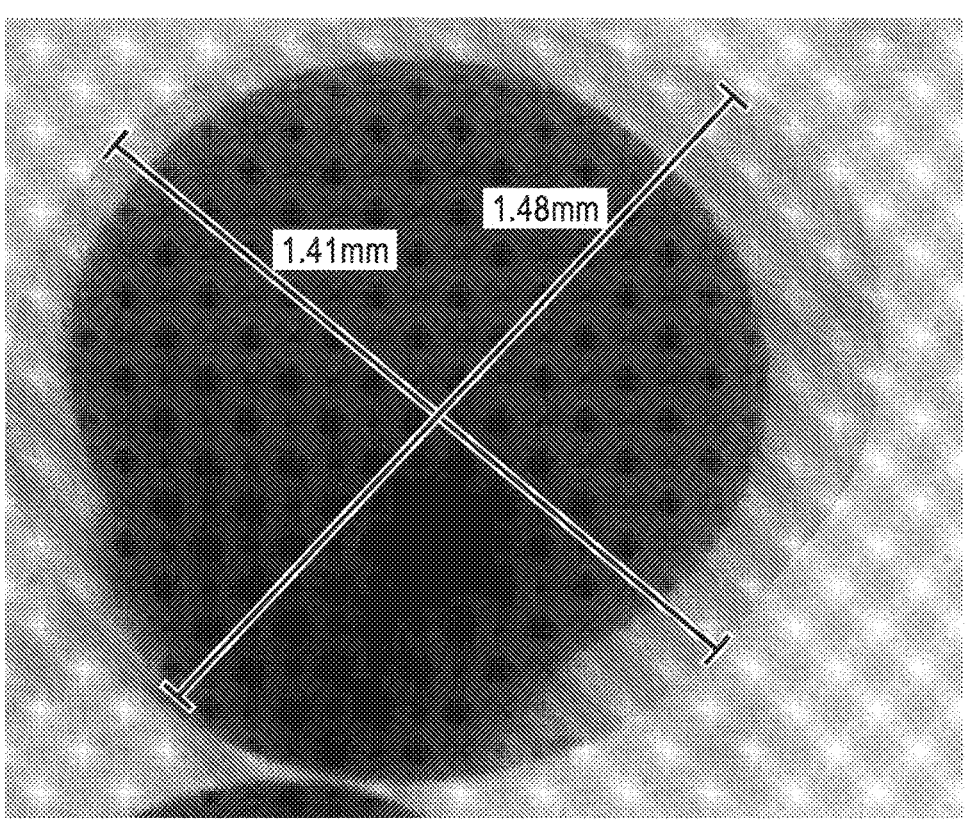
Figure 10B:
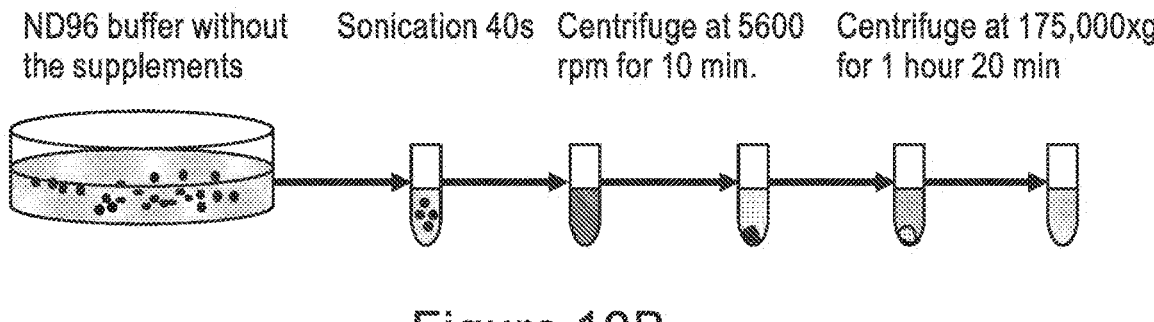

FIGS. 10A-B demonstrate a process for producing OR-containing membrane fragments. FIG. 10A shows crude membrane fractions harvested from *Xenopus* oocytes.

FIG. 10B illustrates the process.

Figure 11A:
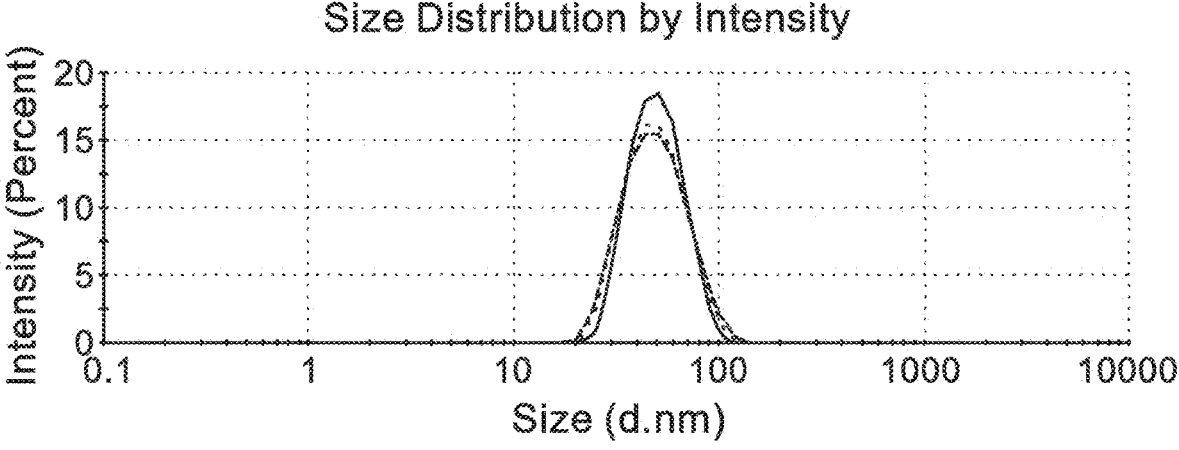
Figure 11B:
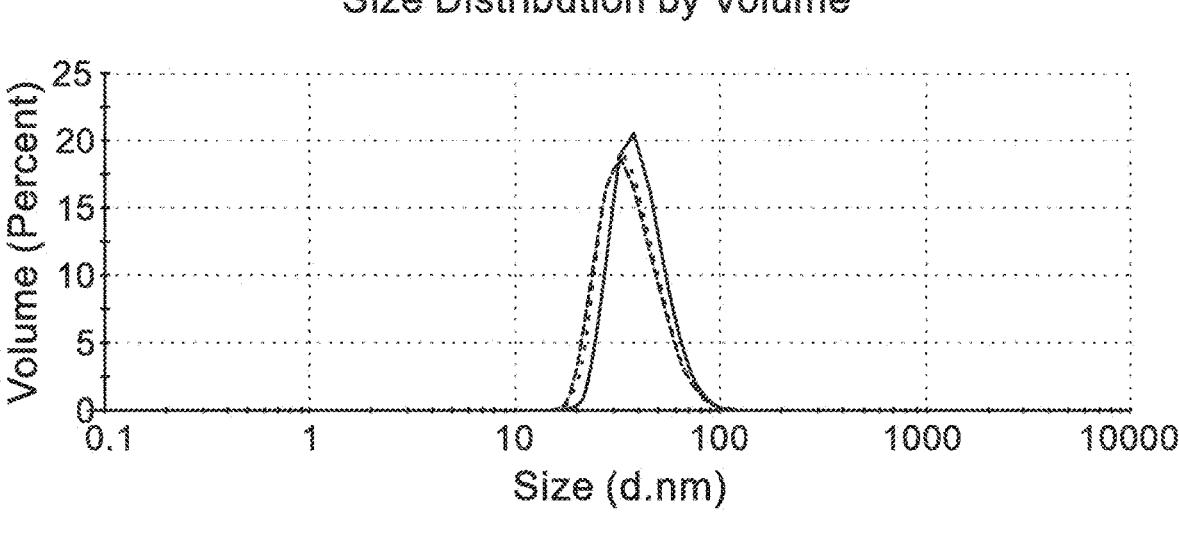

FIGS. 11A-B show dynamic light scattering analyses, demonstrating reproducibility in generating nanovesicles. FIG. 11A demonsartes size distribution by intensity, FIG. 11B shows sizes distribution by volume.

Figure 12B:
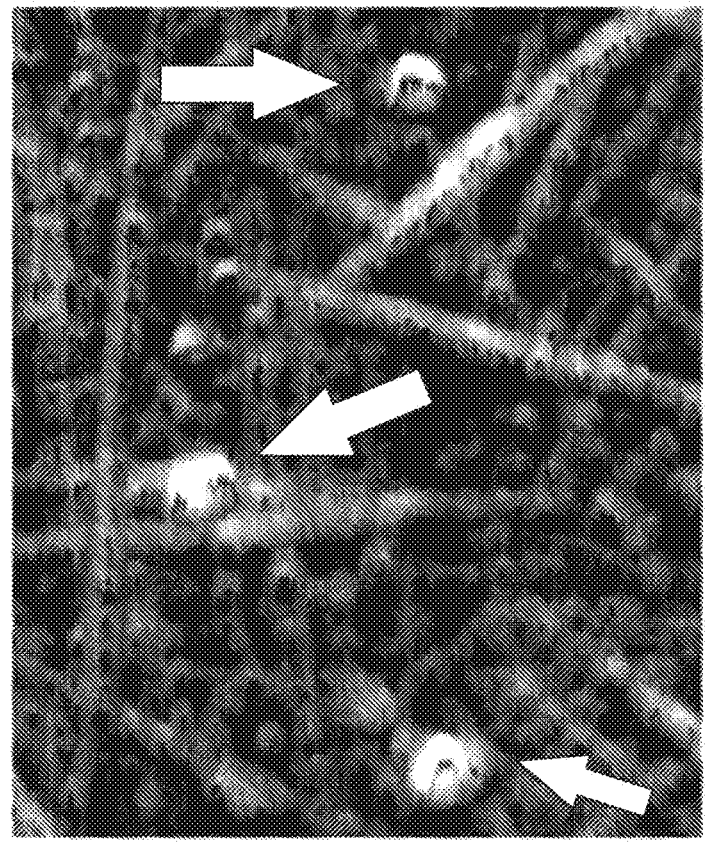
Figure 12A:
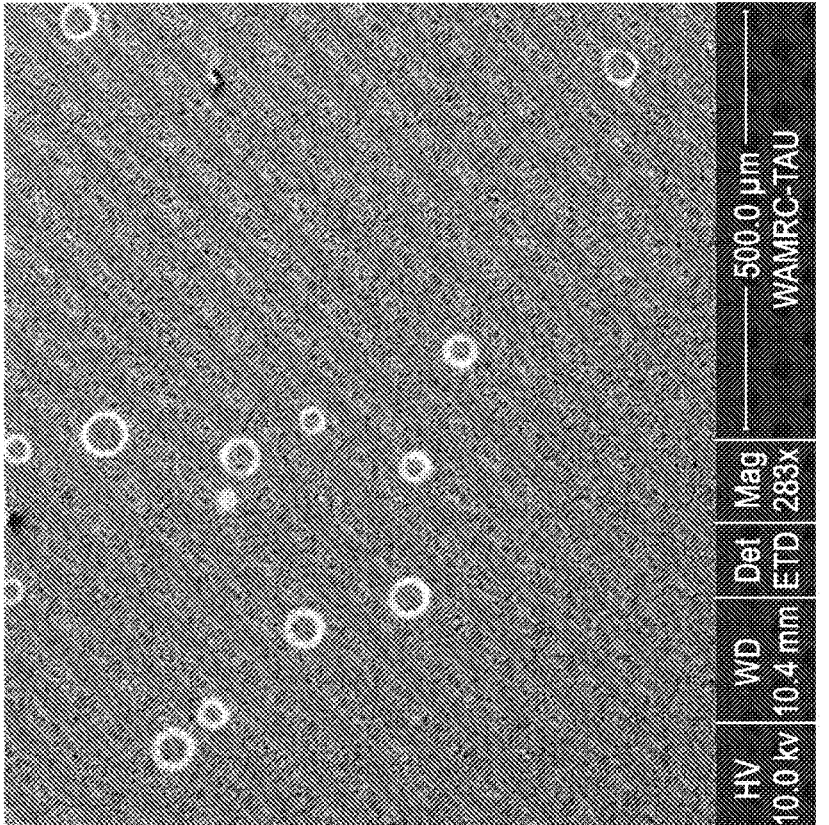
Figure 12C:
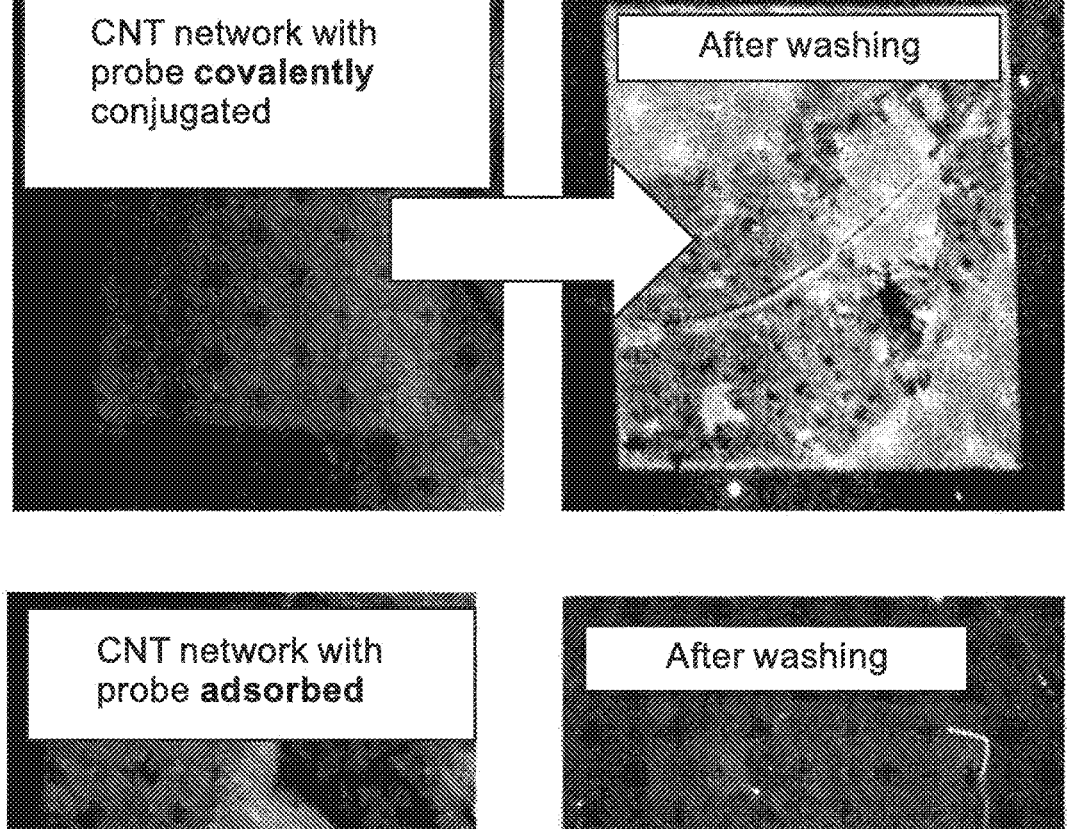

FIGS. 12A-C demonstrate OR-containing membrane functionalization of CNT-FET. FIG. 12A—An SEM image of nanovesicles dispersed of a Si/SiO$_2$ substrate following separation and fragmentation of oocytes membranes. FIG. 12B-AFM image of nanovesicles attached to a CNT network FET device showing the attached nanovesicles (marked with arrows). FIG. 12C—an amine-modified fluorescent probe is covalently attached to a CNT device that was previously modified by diazonium (FBDP) whereas a similar probe is easily removed by rinsing when attached to pristine unmodified CNTs.

Figure 13:
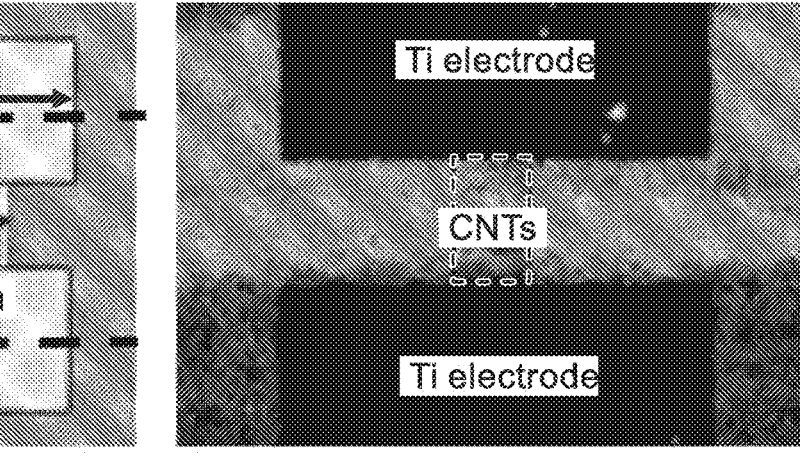

FIG. 13 shows fluorescence response of FITC-NH$_2$ (fluorescent label) coupled to FBDP-modified CNT FET. The attachment performed with flow system where reagents applied to confined region of 200 (w)×280 (h) $\mu$m$^2$ (marked by dashed lines in the left scheme. The scheme is not in scale).

Figures 14A, 14B:
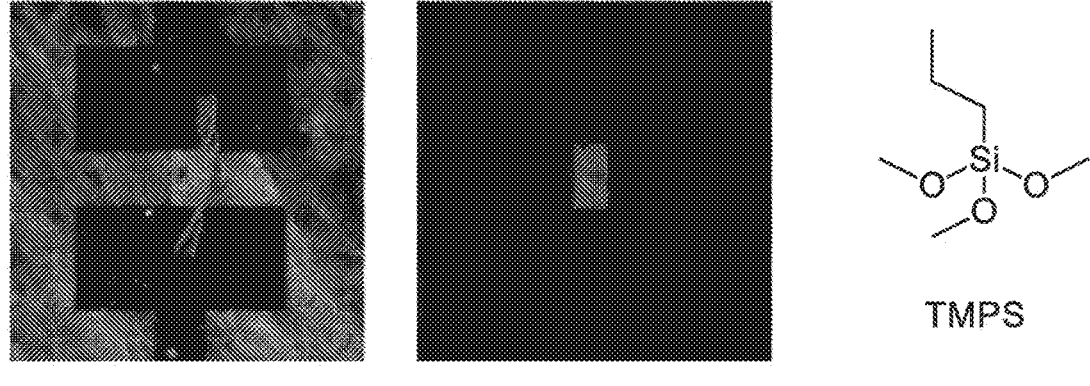
Figure 17A:
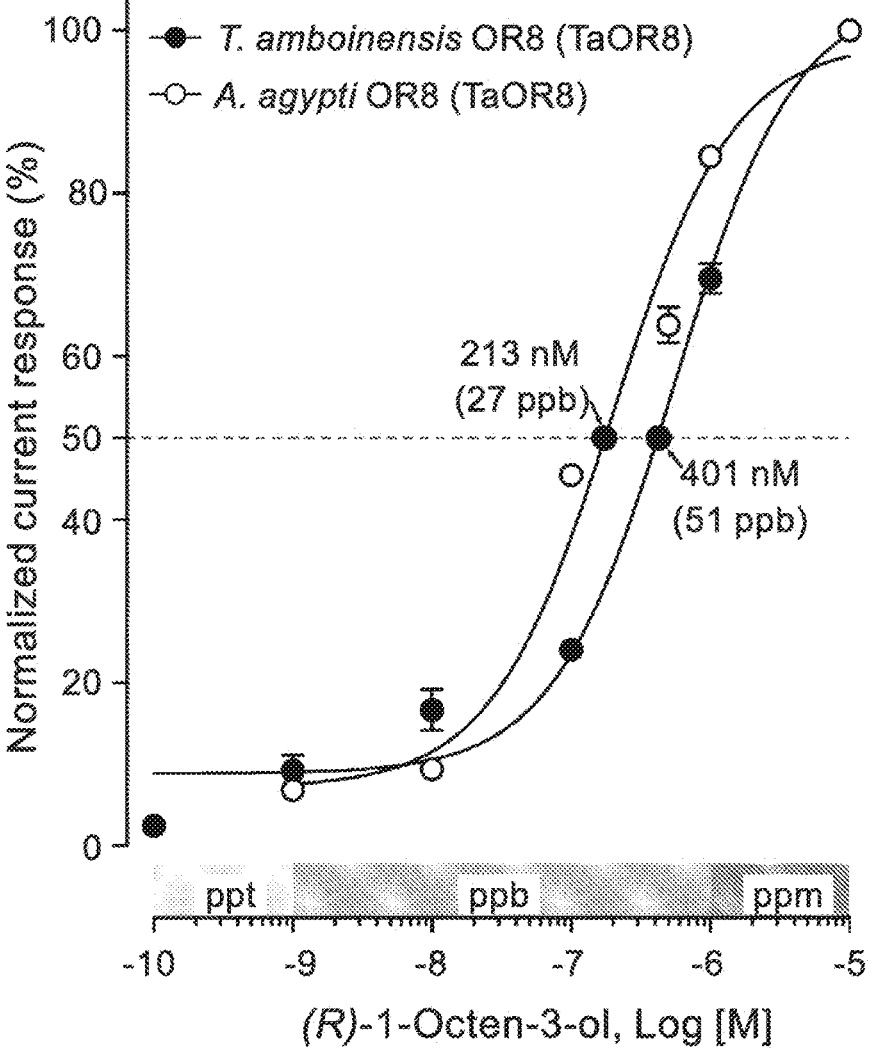

FIGS. 14A-B show selective attachment of Cy3-labled protein to CNT FET. FIG. 17A CNT FET device without TMPS, FIG. 14B CNT FET device pretreated with TMPS. The samples were incubated in solution of 0.1 $\mu$M protein for 90 min at 4° C. and then in PBS for 15 min at 60° C. Fluorescence emission was collected at 570 nm.

Figure 15A:
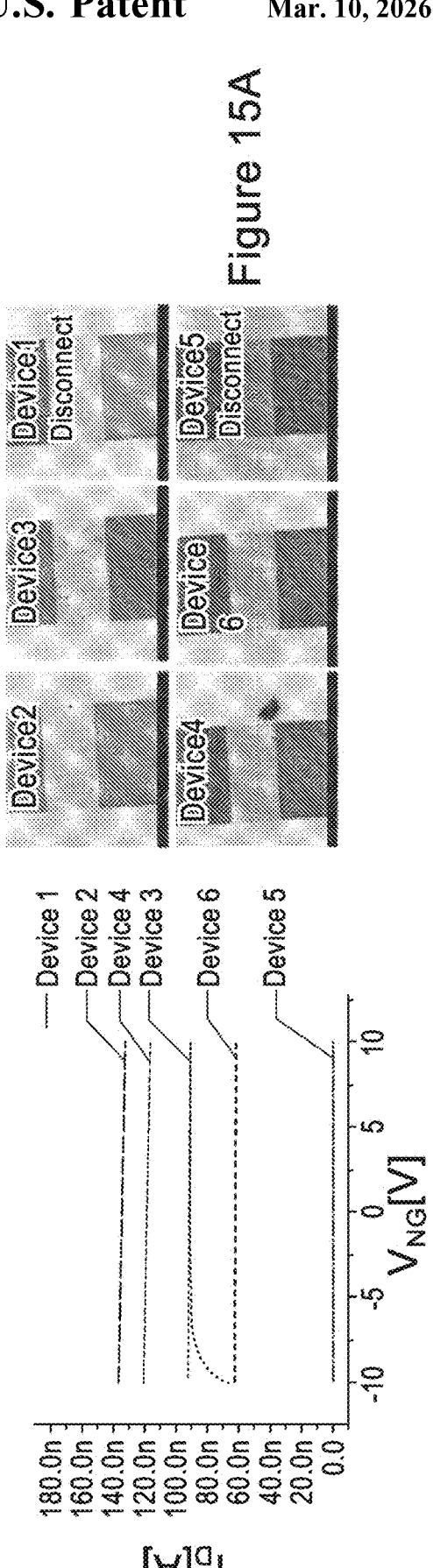
Figure 15B:
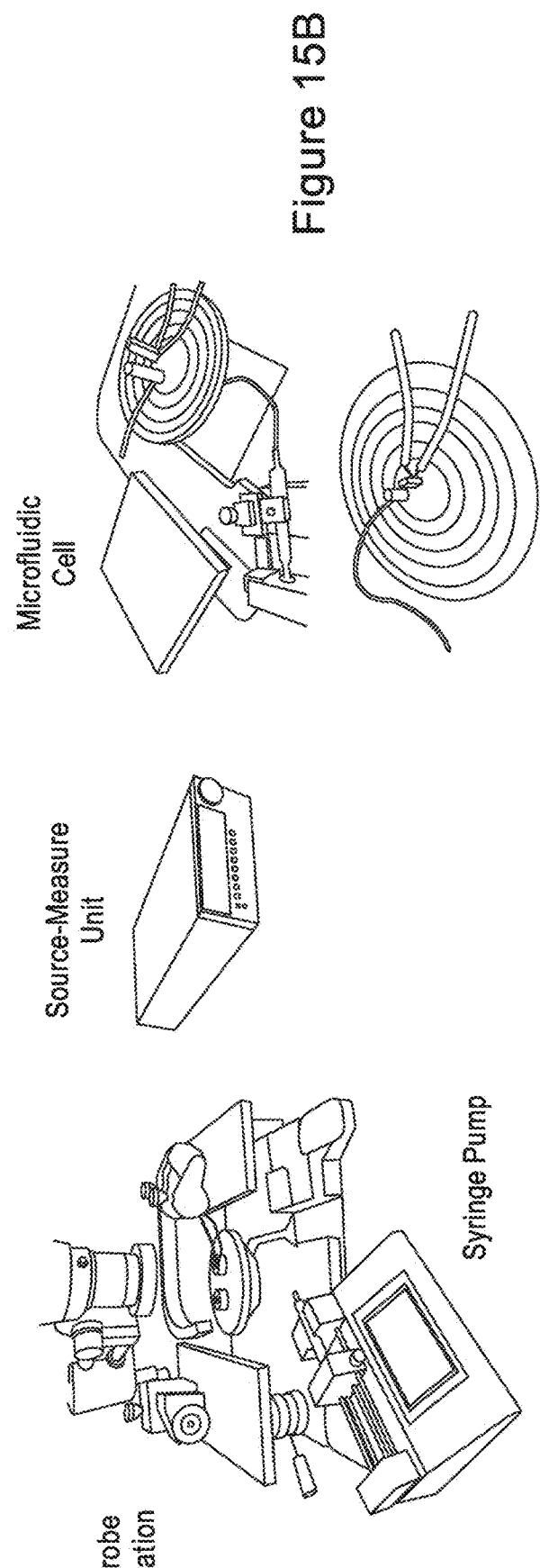

FIGS. 15A-B demonstrate a CNT FET experimental setup and electrical measurements. FIG. 15A—Each device is electrically characterized by measuring its I-V (transconductance) in air (using the Si substrate as a backgate and applying a gate bias of −10V to +10V) or in liquid (electrolytic gate applied by the on-chip Pt gate electrodes from −0.8V to +0.8V and source-drain bias of 100 mV). Shown here are backgated I-V plots of four devices with metallic conductance ranging between 60-140 nA. Two devices had 'opens' (were disconnected). FIG. 15B-Measurement setup includes a probe station and a source-measure unit that enable a thorough electric characterization of CNT-FET devices and additional biosensing measurements. A microfluidic flow cell is stamped on the chip, defining a flow channel of 200 $\mu$m wide. A syringe pump is used to introduce different solutions and reagents.

Figure 16:
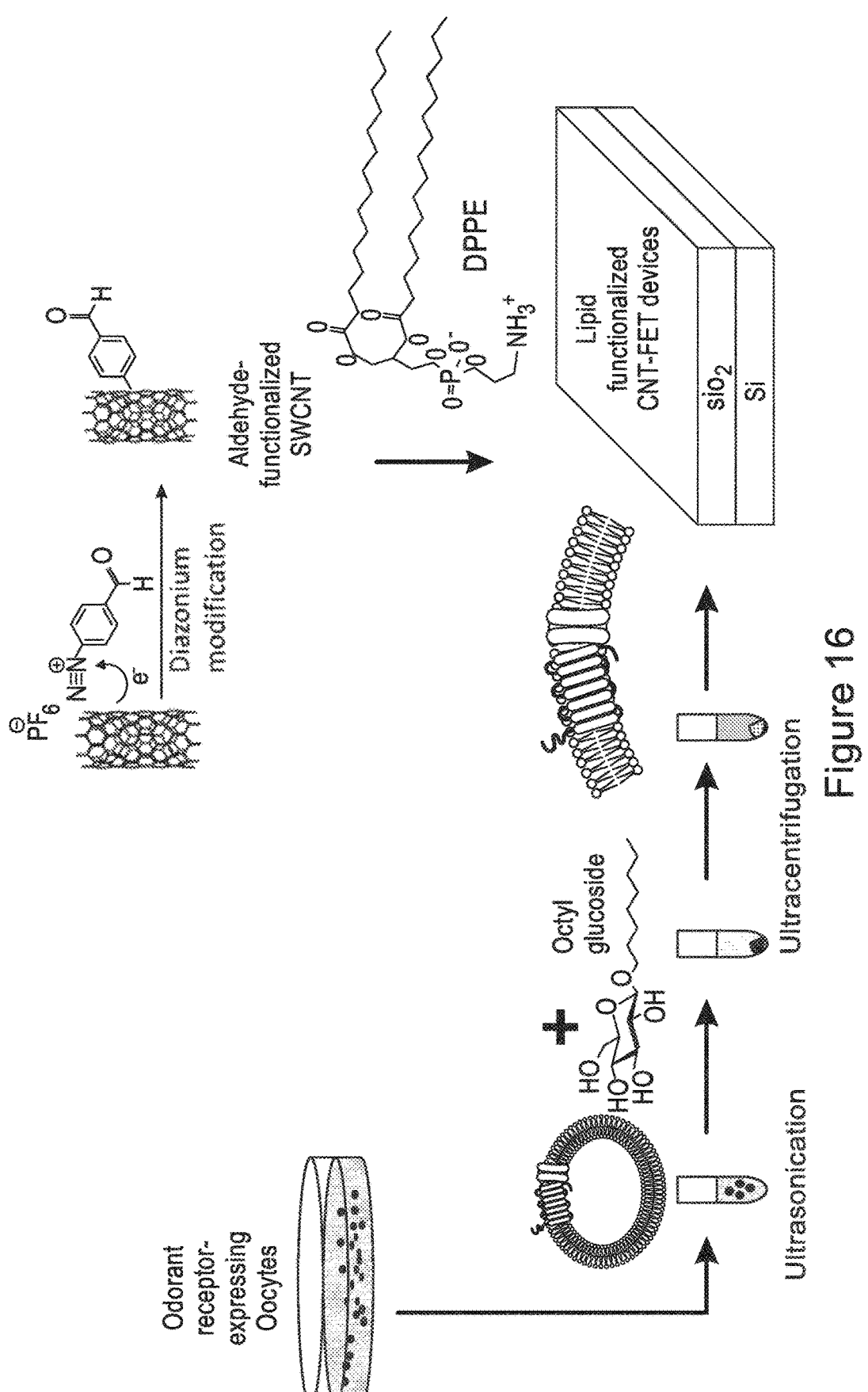

FIG. 16 depicts a biofunctionalization scheme. Amine-terminated phospholipids (DPPE) are tethered to the sidewalls of diazonium modified CNTs, functioning as FET channels, via reductive amination. Subsequently, OR-containing membrane fragments, generated from nanovesicles by a combination of ultrasonication and ultracentrifugation, are attached to the covalently bound phospholipid.

Figure 17B:
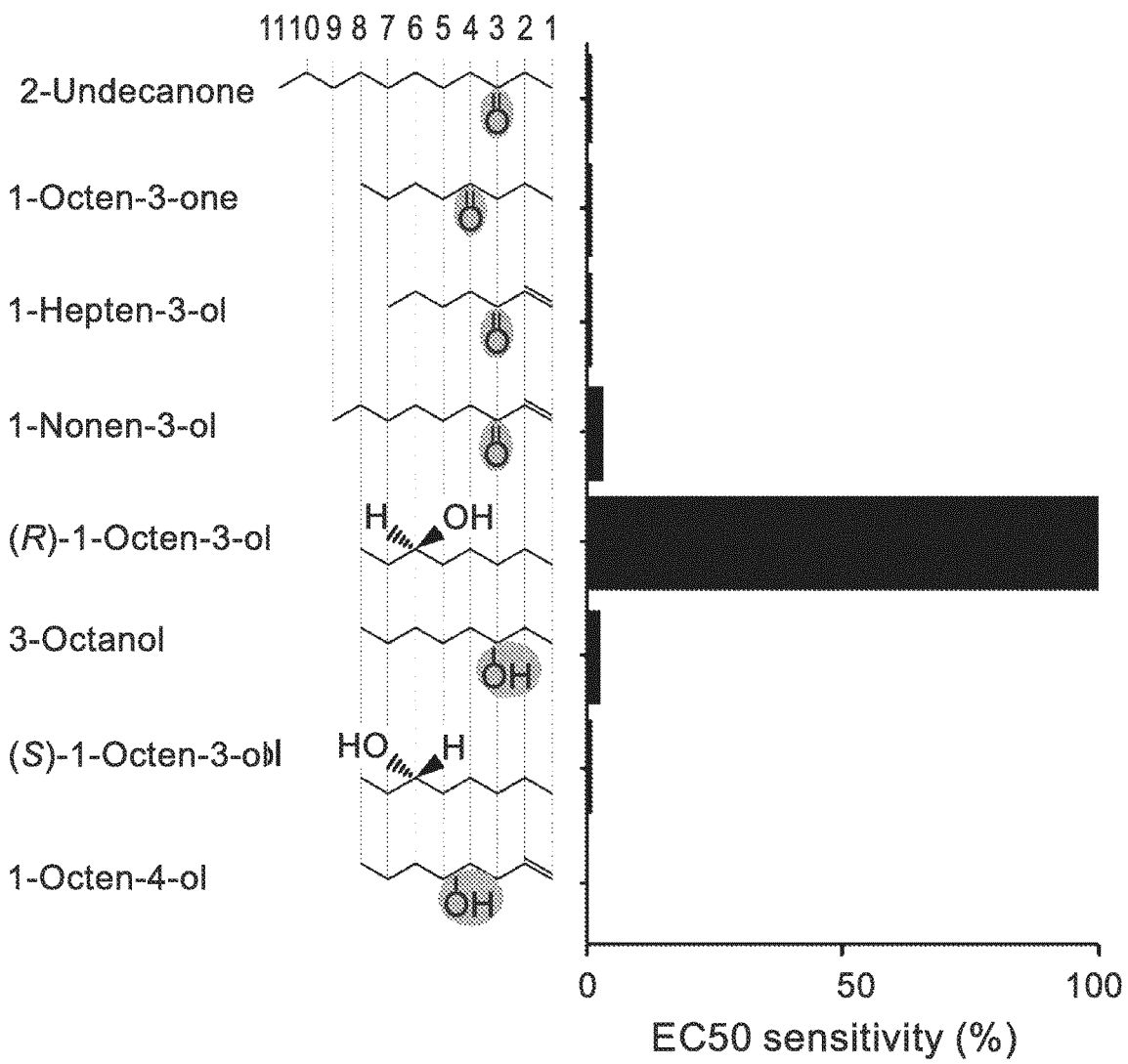
Figure 17C:
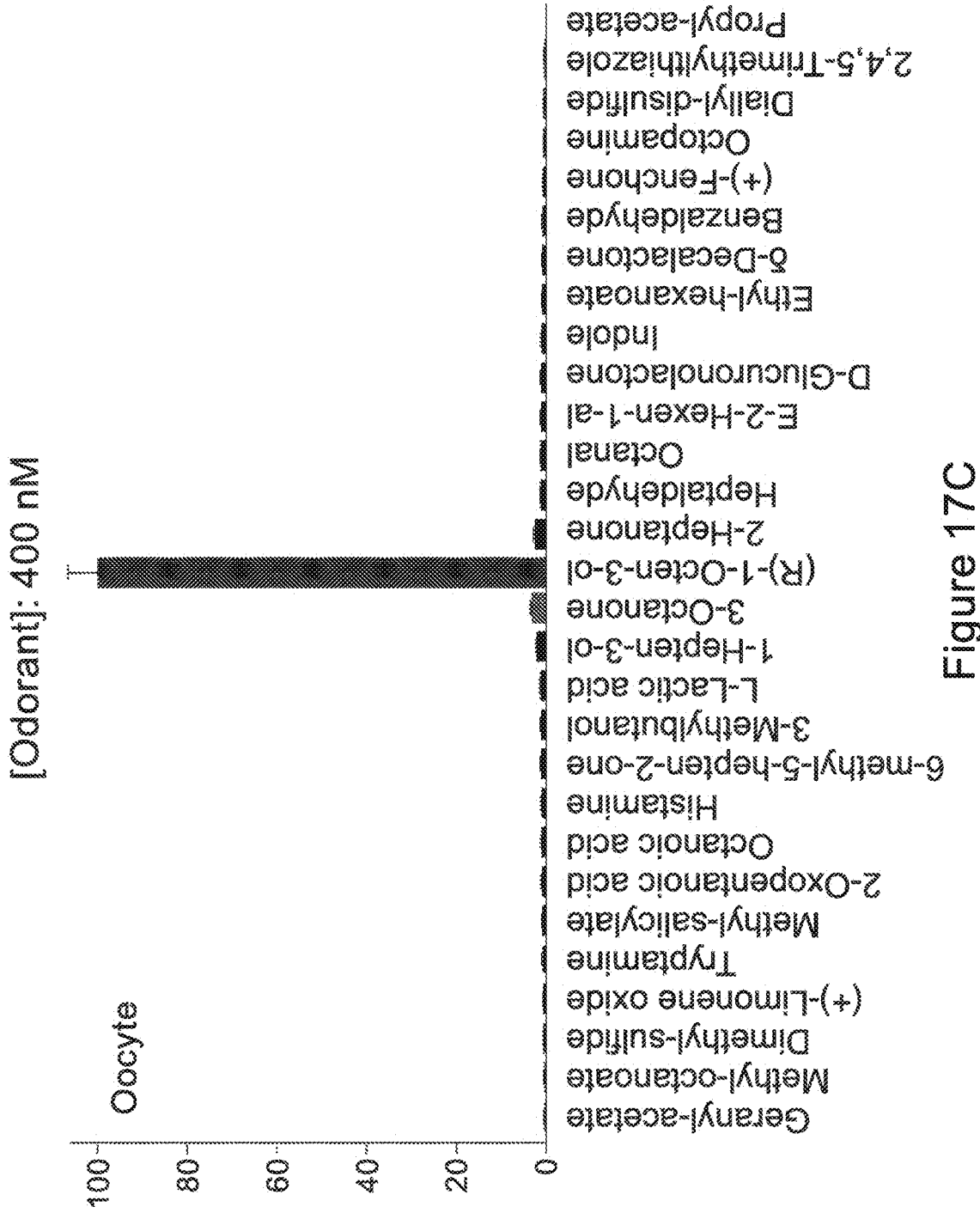
Figure 17D:
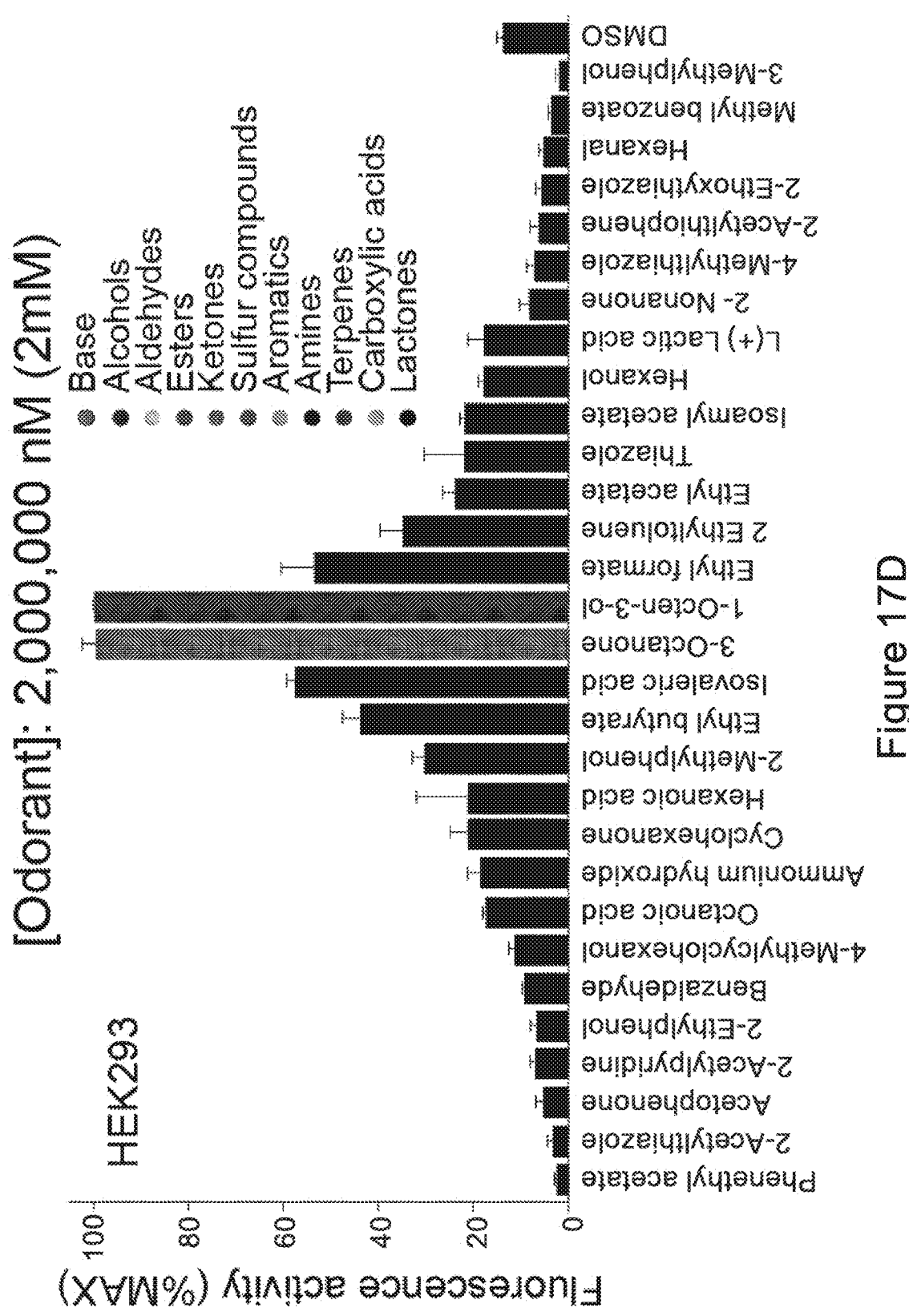

FIGS. 17A-D demonstrate that the mosquito odorant receptor 8 is a highly sensitive and selective octenol receptor. FIG. 17A-OR8 from the mosquito species *Aedes aegypti* (AaOR8) and Toxorhynchites amboinensis (TaOR8) are highly sensitive to (R)-1-octen-3-ol (parts per billion range, ppb). FIG. 17B-OR8 is an enantioselective octenol receptor, distinguishing between the (R)-enantiomer, which is the most abundant form in nature, and the(S)-enantiomer. FIG. 17C—At low concentration (parts per billion range), OR8 is not activated by other chemical classes. FIG. 17D—At high concentration (parts per thousand), OR8 exhibits a broader chemical receptive range.

DETAILED DESCRIPTION OF EMBODIMENTS

The majority of methods for single-molecule studies have only become available in the last decade, with developments in fluorescence-based techniques enabling confocal or TIRF measurement of fluorescence resonance energy transfer (FRET) and force-based methods such as atomic force microscopy (AFM) and optical tweezers. The development of single-molecule observation and manipulation techniques has revolutionized the understanding of many biological processes. Studies of ribosome translation elongation and initiation stages; conformational dynamics of water-soluble and even membrane-protein folding; DNA hybridization and replication; enzymatic catalysis; membrane receptor oligomeriztion GPCR interactions are only a few examples of the recent applications of single-molecule methods.

Established single-molecule methods remain limited by technical obstacles such as difficulties associated with fluorescent labeling, the need to invasively apply external forces to the biochemical system under investigation, limitations in the time resolution with which relatively fast biochemical events can be characterized, and limitations in the total time during which the biochemical reaction under investigation can be observed. For example, Fluorescent probes are fundamentally limited by photobleaching, yielding as few as 10,000 photons for organic dyes and temporal resolution of milliseconds.

Single-molecule bioelectronics offer an exciting new experimental approach based on direct electronic transduction of specific binding into electrons. Direct electronic transduction avoids the use of optics and light sources and allows low-form-factor devices as well as delivers signal levels that are orders of magnitude higher than those achieved with optical detectors.

Bioelectronic detectors comprise an electronic transducer functionalized with a bio-recognition element. Among those, single-molecule field-effect transistors (smFETS) have the unprecedented ability to reach submicrosecond time scales in a noninvasive, label-free study of biomolecular interactions and kinetics, overcoming the limitations of existing techniques. Moreover, devices based on electronic platforms are attractive since they are amenable for miniaturization and can be manufactured using conventional microelectronic fabrication techniques.

Particularly promising are carbon nanotube (CNT) field-effect devices due to their extraordinary properties making them excellent candidates for exposed gate biosensors. CNTs readily form the conducting channel in field-effect transistor (FET) configuration exhibiting an exceptionally high charge carrier mobility and an extremely stable lattice. Most importantly, the density of charge carriers in these 1D materials is sensitive to charges in the environment and therefore the conductance can be modulated by adsorbed molecules. In addition to their biocompatible all-carbon composition, their dimensions are comparable to the size of single biomolecules thus solving the typical problem of 'form factor mismatch' between biology and solid-state interfaces. Finally, CNT-FET devices are attractive since they are manufactured using traditional microelectronic fabrication techniques. As discussed, the transduction mechanism of CNT-FET is based on the significant conductance changes induced by the analyte-nanotube interaction, which implies that this detection approach is label-free. The feasibility of CNT-FET biosensors was demonstrated in the detection of nucleic acids and various protein biomarkers. The lack of specificity and sensitivity often associated with nanotube sensors is a direct result of the fact that the entire 1D conductor is uniformly sensitive to local charge density, rendering the sensor susceptible to nonspecific adsorption anywhere on the exposed surface.

Point-functionalized single-walled carbon nanotube (SWCNT) devices are emerging as an all-electronic, label-free, single-molecule detection platform. This smFET is characterized by a conductance that is sensitive to charges localized within a few Debye lengths of a point defect that is generated on the SWCNT sidewall. This site of functionalization serves as the point of attachment of an SWCNT-tethered probe molecule under study. Under a source-drain voltage bias of several tens to hundreds mV, the current signal level of a typical smFET is tens of nanoampere (nA). smFETs have been successfully used for the study of DNA hybridization and melting kinetics and DNA and protein conformational dynamics.

The proposed smFET comprises Orco or alternatively OR or alternatively a combination of OR-Orco or any other non-nucleic acid receptor molecule derived from animal, plant, insects, bacteria or fungi, as disclosed herein, as a biorecognition element and applies a single-molecule biophysical approach with a custom-developed bioelectronic assay platform in the form of biofunctionalized CNT-FET arrays assembled into a biochip that is interfacing a printed circuit board (PCB). The array will be segmented into specific biosensing regions enabling multiple ligand bindings to be interrogated in real-time. The board may include several dozen or several hundred independently addressable measurement channels that are simultaneously interrogated in real-time. The drain and source potential for each channel are fully tunable and are composed of at least one gain stage and an anti-aliasing filter topology of high order (at least second-order). An FPGA module may be incorporated to interface the hardware and software. The PCB may also include multiplexers, decoders, and analog-to-digital converters. The smFET biochip will be packaged via a chip-carrier and mounted on the board. A designated software enabling real-time measurements and data acquisition may be used. Alternatively, CMOS integrated biochips may be designed, which contain all the required electronics on-chip and can therefore include several thousand to millions smFET devices on a single chip.

A designated microfluidic flow channel is designed, which includes inlets and outlets for the introduction of different reagents. The channel may be fabricated from a silicon elastomer such as poly-dimethylsiloxane (PDMS) or any other biocompatible polymer.

In some implementations of a device of the invention an amine-terminated phospholipid such as 1,2-dipalmitoyl-sn-glycero-3-phosphorylethanolamine (DPPE) is conjugated to the CNT side wall serving as an anchor point, directing the attachment of the membrane fragment, as shown in FIG. 1. By using this new bioelectronic assay, the phase transfer and solubility of volatiles (and their effect on the signal), the electrostatics influence on diffusion-limited capture times and the altering of binding kinetics by an electric field, can be measured. Furthermore, issues of non-specific adsorption and interference are mitigated. The temporal open-closed states distribution of the ion channel can be monitored directly, in real-time. It is suggested that a stronger effect on CNT conductance will be observed due to cationic current in the open state. Despite being incorporated within a lipid bilayer, it is suggested that the channels' transient conformational changes should affect the electric field and modulate the CNT conductance as well.

In another implementation, the nanoscale membrane fragment can contain both constituents of the receptor complex, namely Orco-OR, as shown in FIG. 6. Such configuration combines the sensitivity and intrinsic signal amplification of CNT-FET devices with the unique selectivity of mosquito OR.

Design, fabrication and characterization of CNT-FET array. Chips containing an array of CNT-FET devices are fabricated on a silicon/silicon oxide substrate by either using routinely employed CVD growth techniques or by using drop casting or spin-coating technology combined with photo- or electron beam lithography. Alternatively, devices may be fabricated on any other insulating substrate, such as: metal oxides, polymers etc. said substrate may be of any thickness (provided it is thicker than the deposited metal electrodes, i.e., 90 nanometers) and hardness. As such, substrate may be a flexible material with various degrees of elasticity or plasticity. Spin-cast method is used to randomly place a dilute aqueous single-walled CNT suspension. The nanotube density, spin-cast parameters, nanotube length and electrodes width and gap are optimized in order to maximize the frequency of single CNT crossings. The electrodes pattern (gaps and geometry) are designed to be commensurate with the nanotube length distribution (as shown in FIG. 2A). The optimizations results in single nanotube crossing between each electrode pair. Subsequently, patterning and metal deposition of the source, drain and gate electrodes should result in multiple single CNT-FET devices per chip. In the next step, the devices are characterized using optical and electrical measurements (see FIG. 3). Chips are scanned by SEM and AFM. Raman spectra of individual CNTs are collected as well. Finally, electronic properties are measured by I-V probing in air, using a silicon backgate.

Chips containing multiple CNT-FET devices are exhibiting relatively high conductance (tens to hundreds of nA), as shown in FIG. 3A. The feasibility of spin-cast method to reproducibly generate a high yield of functional CNT-FETs has been shown. An example of a CVD-grown chip as compared with a spin-cast chip is shown in FIGS. 3A and 3B.

Also shown are AFM images, which help to confirm the CNT diameter. A CNT resonant Raman spectroscopy analysis measures the ratio of the D band ("disorder mode") to the tangential G band, which serves as an indicator to the number of intrinsic CNT defect. In addition, the electronic structure is elucidated by analyzing the G mode components. The radial breathing mode (RBM) is collected, as well, indicating the CNT diameter. Only CNTs demonstrating no scattering at the D band (apparent "pristine" nanotubes) are used in the constructions of the devices. Typical Raman spectra of a CNT grown on $Si/SiO_2$ is shown in FIG. 3C.

A preliminary study was based on CNT network FET devices (CNTN-FET).

Such design enables chip production at very high yields. We have optimized the parameters for generating a reproducible and homogenously dispersed CNT layer on a $Si/SiO_2$ chip. Briefly, pure, as-prepared CNT suspension (containing pre-sorted SWCNTs with a narrow size distribution) was used to coat a $Si/SiO_2$ substrate by a brief sonication followed by a spin-casting method while adjusting concentration, solvent type, incubation period, sonication power and time. The layer was characterized by SEM, AFM and Raman, as shown in FIG. 7A. Titanium source and drain electrodes and platinum pseudo-reference gate electrodes were photolithographically patterned and deposited above the CNT layer. An Illustration of the preliminary design is shown in FIG. 7B. For each FET device, a CNT conducting channel was defined (as shown in FIG. 7C) and the remaining CNT layer was plasma etched. The resulting devices demonstrated homogenous CNT density across the chip (as shown in the SEM image of FIG. 7D). Devices were further characterized structurally and electrically as previously mentioned.

Additional images of a fabricated chip that comprises 90 nm thick titanium source and drain electrodes and platinum gate electrodes, are presented in FIG. 8A-B. Additional SEM image is presented in FIG. 8C.

Orco expression, electrophysiology and purification. Supply of Orco-rich membranes will be predicated on the functional validation carried out using the two-electrode voltage clamp of *Xenopus* oocytes expressing this receptor. Expression and recordation of the pharmacological activity of mosquito odorant receptor complexes (ORx-Orco) in *Xenopus* oocytes has been studies extensively. This technique to study the agonist activity of Orco agonists (e.g., VUAA1) and antagonists (e.g., octadienal and carvacrol) (as shown in FIG. 4A) or associated with ORx has been achieved. In some cases Orco rather than ORx was used in order to reduce potential pitfalls associated with OR complexes. In some cases, ORx alone is not functional without its co-receptor chaperone. Two types of expression vectors adapted to *Xenopus* oocyte expression are used. pSP64DV was used to record currents reaching over 1 µA from Orco exposed to VUAA1, indicating high protein levels (FIG. 4B). Considering the objective to extract Orco-rich membrane fragments less than <50 nm in length, receptor density should be sufficient to ensure that these short fragments contain Orco. To evaluate Orco density, this gene was expressed using the pCMV6-AC-mKate expression vectors (Origene), or other tagged version. This plasmid functions well in *Xenopus* oocytes and adds a constitutively fluorescent mKate2 tag on the C-terminus of the protein of interest (here Orco) that can be directly or indirectly (fluorescence immunohistochemistry) detected by confocal scanning laser microscopy. If the C-terminal tagging compromises Orco function, the N-terminal mKate2-tagging vector instead (pCMV6-AN-mKate, Origene) will be required.

Orco is synthesized from linearized pSP64DV expression vectors using the mMESSAGE mMACHINE™ T7 ULTRA Transcription Kit (Life Technologies). Capped Orco RNA is injected in stage V-VI oocytes, incubated for 3-5 days and exposed to the agonist VUAA1 based on protocols published elsewhere.

During a typical recording session, individual oocytes are exposed to a single concentration of $10^{-4}$ M of VUAA1 in order to (i) limit the exposure of ORco to this agonist and (ii) to identify the oocytes with highest Orco expression levels. Qualified oocytes are collected to isolate and evaluate the density of membrane receptor complexes.

The isolation of small oocyte membrane patches is carried out via lysis, homogenization and a subsequent differential ultracentrifugation in a sucrose gradient. Similar protocols were originally developed as sample preparation methods for both confocal microscopy and high-resolution AFM analysis of *Xenopus* oocytes membranes. It was shown that patches of solubilized planar oocyte membranes with lateral dimensions<500 nm and thickness of 3-5 nm were generated and retained for prolonged periods.

Chemical modification and bio-functionalization. Different versions of CNT-FET sensors have attempted to detect biomolecules adsorbed onto pristine and coated CNTs. Transient non-covalent attachment has been pursued using pyrenes or porphyrins exploiting π-π stacking of these molecules with the CNT carbon lattice. The lack of specificity and sensitivity usually associated with nanotube sensors is a direct result of the fact that the entire 1D conductor is uniformly sensitive to local charge density, rendering the sensor susceptible to nonspecific adsorption anywhere on the exposed surface. Introducing a defect onto the CNT surface localizes this sensitivity, making the CNT only sensitive to charge density in the region near the molecule under study. This defect can, in turn, be used to covalently link a biomolecule at the point of charge sensitivity of the transducer. The resulting device can be used to measure time-resolved changes in the conductance of the nanotube that arise from changes in scattering in the 1D channel caused by Coulomb interactions between the biomolecule and the defect. Covalent attachment strategies also offer desirable permanent tethering of the biomolecule. Among all methods, the reaction of CNTs with diazonium salts has been widely studied, becoming one of the most popular routes of CNT covalent functionalization. Covalent modification impart a measurable resistance change in the device by converting carbon bonding from $sp^2$ to $sp^3$ orientation. Controlling the reaction electrochemically is feasible by applying solution bias to promote or inhibit electron transfer between the charged diazonium and the CNT lattice (the associated resistance change due to the addition of one $sp^3$ defect has been argued to be on the order of: $h/4e^2$). The coupling of 4-formylbenzene diazonium hexafluorophosphate (FBDP), which contains an orthogonal aldehyde functional group, later used for bio-conjugation is electrochemically regulated. A subsequent tethering of a linker molecule (e.g., DPPE) is carried out via reductive amination, as shown in FIG. 5A. This covalently attached lipid serves as an anchor directing the attachment of an Orco-containing membrane fragment. The major advantages of this functionalization strategy are: i) locating the interrogated biomolecule in intimate contact with the charge sensitive region; ii) locating the biomolecule within a Debye sphere around the CNT sidewall (the requisite proximity scales with a Debye screening length) thus enabling electrostatic modulation of Orco binding and conformational changes; iii) ensuring optimal orientation of Orco-containing membrane fragment with the CNT sidewall, perpendicular to the cation flow in the channel; iv) enabling a non-transient, stable Orco-CNT hybrid for prolonged measurements. Studies of SLB (suspended lipid bilayers)-CNT hybrids have shown promise in electrical detection of target binding. The shift in the transistor threshold ($\Delta V_e$), due to additional charges, was shown to be related to its charge density by:

$$\sigma = 2\Delta V_e \varepsilon_W \varepsilon_0 / \lambda_d$$

where $\varepsilon_W$ is the dielectric constant of water and $\lambda_d$ is the Debye length.

The directed attachment of the as-obtained membrane fragments to the covalently bound phospholipid largely depends on the membrane's planar configuration. It is therefore paramount to understand the conditions allowing for a bilayer membrane fragment to maintain planar configuration in solution. The dynamics of lipid bilayer vesicles has been extensively studied using SLB as a model. Vesiculation or planarization of bilayer membrane is dependent on the free energy of each state, which is in turn, dependent on the entropy of closure and the membrane bending and contour (edge tension) free energies. The bending energy per unit area is given by:

$$e_b = \frac{1}{2}\kappa(c_1 + c_2)^2 + \bar{\kappa}(c_1 c_2)$$

where $\kappa$ is the bending rigidity and $\bar{\kappa}$ the bending modulus, which indicates the membrane malleability. The principal curvatures, $c_1 + c_2$ are the eigenvalues of a curvature tensor that describes the local shape of the membrane. The structural origin of edge tension ($\gamma$, the contour energy per unit length) arises from the deformation of the lipids that occupy the edge. It has been suggested that the stability of a planar or a spherical lipid bilayer can be described by:

$$\alpha = (\gamma/\kappa_b)(A/\pi)^{0.5}$$

where $\gamma$ is the edge tension, $\kappa_b = 2\kappa + \bar{\kappa}$ describing the bending free energy and A the area of the membrane. Using empirical values of $\kappa_b \sim 5\text{-}25 \ k_b T$ ($k_b$ is Boltzmann constant) and $\gamma = 1\text{-}2 \ k_b T/l$ (l is length), it follows that planar lipid bilayers<50 nm are sufficiently stable. In addition, incubation of the membrane fragments with the CNTs above their transition temperature may further facilitate their correct orientation. Consequently, small planar Orco-containing membrane fragments will be tethered to the CNT sidewall displaying an angular position that is defined (and limited) by the rotational freedom of the CNT-bound lipid tail. It should be noted that although the vesicular configuration is less likely to conjugate to the CNT-phospholipid (since it depends on the vesicle rupture), the closure of a planar bilayer post-conjugation, on the other hand, will not necessarily compromise signal transduction and device performance.

Moreover, other orientations that result in the positioning of the Orco ion channel parallel to the CNT sidewall (i.e. due to adsorption of the lipid tails to the CNT lattice) should still be able to effectively modulate the device conductance, as long as the ligand-induced ionic current flows within the Debye sphere.

A single tethered Orco channel affects a measurable conductance change in any given device due to the sensitivity of the 1D channel to electrical charges in the vicinity of the defect as previously described. In fact, the ability of the CNT-FET to resolve the molecular charge of a single nucleotide (~0.1e) has been demonstrated using a similar device and a tethered nucleic acid.

In some embodiments, the chemical modification and bio-functionalization steps will be carried out via microfluidic channels (patterned in a Polydimethylsiloxane (PDMS) elastomer stamping).

Preliminary results. Previously, we have demonstrated our ability to electrochemically control the extent of a CNT-FET diazonium (FBDP) functionalization to a resolution of a single $sp^3$ defect. Electrochemical control over FBDP functionalization of SWCNT was attained by shifting its Fermi energy (via application of voltage bias), thereby increasing electron density near the surface. The extent of sidewall modification was demonstrated by repeated I-$V_{1g}$ (liquid gate) measurements following consecutive exposures to FBDP, as shown in FIG. 5B. Moreover, the reaction can be monitored in real-time by measuring the conductance upon FBDP exposure (I-t traces). In this case, as shown in FIG. 5C, current drops originating from the diazonium reaction are clearly visible. These drops are quantized and represent the generation of a single $sp^3$ defect, as evident, for example, from the altered Raman features and AFM imaging shown in FIGS. 5D and 5E. The rehybridization of $sp^2$ to $sp^3$ eliminates current paths in the 1D channel resulting in the observed decreased conductance.

The diazo compound formylbenzenediazonium hexafluorophosphate (FBDP) was synthesized from 4-aminobenzaldehyde in acidic solution at $-10°$ C. as depicted in FIG. 9A. The product was purified by filtration and characterized by FT-IR (FIG. 9B). The spectrum features the IR stretch bands of the aldehyde group, the para-substituted benzene group, and importantly, the formed diazonium group at 2300 cm$^{-1}$.

In addition, in a preliminary study, OR-containing membrane fragments were obtained by a combination of ultra-sonication, ultracentrifugation and detergent treatment, and attached to a chemically modified CNT sidewall. Briefly, crude membrane fractions were harvested from *Xenopus* oocytes (FIG. 10A). Typically, oocytes can be harvested 2-5 days after RNA injection. Batches of 10-15 oocytes are homogenized in 1 mL of HEDP buffer (100 mM HEPES, 1 mM EDTA, pH 7.6 with NaOH) plus 5 µL of protease inhibitor cocktail performed at $4°$ C. Homogenates are centrifuged at 5600 rpm for 10 min. the supernatant obtained from step is pipeted into two 7 mL of ice-cold 15% sucrose in HEDO buffer, centrifuged at 175,000 g for 1.5 hours. The process is illustrated in FIG. 10B.

The inventors' ability to reproducibly generate nanovesicles (that are ~ 30 nm in size, is proven as indicated by dynamic light scattering analyses, shown in FIG. 11A-B.

These generated nanovesicles (Also scanned by using electron microscopy, as shown in FIG. 12A) were subsequently attached to CNT devices (as shown in the AFM image in FIG. 12B). We have further demonstrated the robustness of our covalent bonding strategy by conjugating a fluorescent probe to an FBDP-modified CNT device, as shown in FIG. 12C.

Receptor attachment with flow system. We proceeded to establish conditions for receptor attachment with flow system. With this setup, the sequential modification of the CNTs with FBDP and receptor coupling via reductive amination are performed by flowing the reagents through 200 (w)×280 (h) µm$^2$ channel that confines the entire CNTs region and partial areas of the Ti electrodes (see depiction in FIG. 13). As shown in FIG. 13, in addition to the covalent attachment of FITC-NH$_2$ (fluorescent label) to the CNTs, direct adsorption to the bare SiO$_2$ is prominent.

We have previously shown that prolonged incubation at elevated temperature enabled effective clearance of FITC-NH$_2$ from the bare SiO$_2$ surface. However, in order to achieve selective attachment without the necessity of rigorous washing and sample heating, we have first activated the SiO$_2$ surface with propyltrimethoxysilane (TMPS). We expect that in addition to create a physical barrier, formation of hydrophobic surface by the propyl residue will repel incoming polar and/or charged molecules such as ORs. FIG. 14 demonstrates the implementation of our approach for attaching a model protein labeled with Cy3 fluorophore to CNT FET devices. FIG. 14A shows a device that was incubated in protein solution without TMPS activation, and FIG. 14B shows a similar device that was treated with TMPS prior to incubation with the protein. While prominent amount of protein was adsorbed to the bare SiO$_2$ surface (not treated with TMPS), the TMPS treated device shows selective adsorption to CNTs.

Experimental setup, PCB design and measurement platform. The feasibility of the proposed bioelectronic constructs can be demonstrated by probing individual devices with a commercially available electronic measurement setup (probe station). The biochips, however, are designed to interface a custom designed PCB enabling a highly efficient and convenient measurement. The PCB may include several dozen or several hundred independently addressable measurement channels that are simultaneously interrogated in real-time. The drain and source potentials for each channel are fully tunable and are composed of at least one gain stage and an anti-aliasing filter topology of high order (at least second-order). An FPGA module may be incorporated to interface the hardware and software. The PCB also includes multiplexers, decoders, and analog-to-digital converters. The biochip will be packaged via a chip-carrier and mounted on the board.

A designated software enabling real-time measurements and data acquisition may also be used. Alternatively, CMOS integrated biochips may be used, which contain all the required electronics on-chip and can therefore include several thousand to millions smFET devices on a single chip.

A designated microfluidic flow channel may also be present, which includes inlets and outlets for the introduction of different reagents. The channel may be fabricated from a silicon elastomer such as poly-dimethylsiloxane (PDMS) or any other biocompatible polymer.

Measurement matrix: a measurement matrix may be formed by filling the flow cell with an electrolytic buffer or an electrically conductive hydrogel or electrically conductive polymer thus providing the Orco-containing membrane with the optimal conditions, ensuring higher activity and sensitivity. Solubilized ligands may be used during the preliminary data collection. Addition of small volume of organic solvent (e.g., DMSO) will enable the dissolution of the rather hydrophobic small organic compounds. The diffusion coefficient of VOCs in air is larger by orders of magnitude compared to water. Mass transfer of a VOC across air-water interface is dependent on its dissolution rate constant ($k_d$), surface area of the air-water interface ($A_{aw}$), the maximal solubility of the VOC ($C_{wmax}$) and the water volume ($V_W$) such that:

$$\ln\left(\frac{S_w - C_w(t)}{S_w}\right) = -\frac{A_{aw}k_d C}{V_w}, \text{ where } S_w = C_{wmax} = C_{amax}/H_c,$$

where $C_{amax}$ is maximal VOC concentration in the air phase and He is Henry's solubility constant. The VOC dissolution rate constant ka can hence be estimated from the slope of a ln ($S_W-C_W/S_W$) versus t plot . . .

A designated set up for air sampling will be fitted. A simple air suction system will be installed, comprising a miniature fan and a filter (for dust and airborne small particles). Sampled air will be channeled through tubing into the microfluidic channels to introduce VOC analytes.

In a preliminary study measurements were performed by individually interrogating each device with an electronic measurement setup. These measurements include I-V and noise characteristics, and time traces. The biochip is stamped with a PDMS microfluidic flow cell placed directly above the devices, which includes inlets and outlets for the introduction of different reagents. A picture of the experimental setup is shown in FIG. 15B.

A schematic illustration of the chemical modification and biofunctionlaization strategy is presented in FIG. 16: a native OR, embedded in a nanoscale membrane fragment ("nanosomes" is covalently attached (via diazonium defect) to an amine-terminated phospholipid (DPPE) used as an anchor point.

Disease-causing molds affect the livelihood and food security of millions of people worldwide. With the stakes so high, reducing the impact of these pathogens is paramount. 1-Octen-3-ol or mushroom alcohol is a microbial volatile organic compound (mVOC) released by molds, which is an early warning signals of environmental hazards, neurodegenerative diseases, food contaminations and fruit diseases. It is also a food additive or a flavoring agent that has important uses in process manufacturing. The (R) enantiomer of 1-octen-3-ol is one of the most common and abundant VOC released by fungi such as *Penicillium* spp. and *Aspergillus* spp. molds.

In studies of mosquito OR, the inventors' have shown that mosquito odorant receptors known as OR8 are activated by (R)-1-octen-3-ol in the parts per billion range (FIG. 17A). Indeed, any modifications of the double bond saturation, side chain length, chiral center position, or functional substitution of the (R)-1-octen-3-ol chemical structure is sufficient to prevent OR8 from being activated (FIG. 17B). At this concentration range, OR8 exhibits a narrow molecular receptive range (FIG. 17C). However, at higher odorant concentrations, OR8 exhibits a broader odorant tuning profile (FIG. 17D), being activated by a wider range of chemical structures.

These studies established OR8 as a sensitive enantioselective odorant receptor, whose narrow odorant tuning is optimal in the nanomolar range, which is excellent in the field of receptor pharmacology. This receptor is among the most selective reported odorant receptor, whose activation plummets when exposed to any slight modification of the chemical structure of (R)-1-octen-3-ol. OR8 is the epitome of receptor selectivity, being able to reject any slight modification on the (R)-1-octen-3-ol backbone manifesting in complete activation shutdown (FIG. 17B). At a low concentration the receptor is specific to (R)-1-octen-3-ol (FIG. 17C), which is a desirable property for the purpose of using this receptor to detect early signs of microbial contamination or presence. However, OR8 selectivity diminishes at higher odorant concentrations, exhibiting a broader molecular receptive range (FIG. 17D).

The invention claimed is:

1. A bioelectronic sensor for detecting the presence of at least one volatile organic compound (VOC), the sensor comprising a single carbon nanotube (CNT) to which a single insect receptor derived from mosquitos or flies is covalently immobilized via a linker moiety, wherein association of the VOC to said receptor allows for a measurable electric field effect.

2. The sensor according to claim 1, wherein the at least one VOC is indole.

3. The sensor according to claim 2, wherein the indole is selected from indole (1H-indole), skatole, indole-3-butyric acid, indole-3-acetic acid, indole-, 3-carbinol, tryptophan and beta carboline.

4. The sensor according to claim 1, wherein the receptor is mosquito-derived indolergic odorant receptor (OR).

5. The sensor according to claim 1, implemented into a biochip interfacing a printed circuit board (PCB).

6. The sensor according to claim 5, configured as an array of sensors that are assembled into a biochip interfacing a printed circuit board (PCB).

7. The sensor according to claim 6, wherein the array is segmented into specific biosensing regions enabling multiple ligand bindings to be interrogated in real-time.

8. The sensor according to claim 5, comprising one or more measurement channels configured for simultaneous real-time interrogation.

9. The sensor according to claim 8, wherein each measurement channel is appended with a drain electrode and a source electrode.

10. The sensor according to claim 5, wherein the PCB further comprises at least one element selected from multiplexers, decoders and analog-to-digital converters.

11. The sensor according to claim 1, wherein the CNT is selected from single-walled carbon nanotube (swCNT), double-walled carbon nanotube (dwCNT) and multi-walled carbon nanotube (dwCNT).

12. The sensor according to claim 1, wherein the receptor is a single OR9 receptor or Orco covalently associated to a single swCNT molecule.

13. The sensor according to claim 1, wherein the single insect receptor derived from mosquitos or flies is a membrane bound receptor, said receptor comprising a membrane containing said membrane bound receptor.

14. The sensor according to claim 1, wherein the linker moiety is selected to control alignment of the single insect receptor.

15. The sensor according to claim 1, wherein the linker moiety is an amine-modified phospholipid conjugated to a defect site on the CNT via an amine group.

16. The sensor according to claim 15, wherein the amine-modified phospholipid comprises lipid chains functionally aligning the single insect receptor or membrane comprising same through hydrophobic interactions.

17. The sensor according to claim 1, wherein the linker moiety is selected from peptides, phospholipids, polymers, conductive polymers, hydrophobic polymers, and hydrophilic polymers.

18. A bioelectronic sensor for detecting presence of at least one indole, the sensor comprising a single carbon nanotube (CNT) to which a single mosquito-derived indolergic odorant receptor (OR) is covalently immobilized via a linker moiety, wherein association of the at least one indole to said receptor allows for a measurable electric field effect.

19. The sensor according to claim 18, wherein the OR is selected from OR2, OR9, OR10, OR co-receptor (Orco) or a combination thereof.

20. The sensor according to claim 19, wherein the OR is OR9 or OR9 co-receptor.

21. The sensor according to claim 18, wherein the OR is OR8.

22. The sensor according to claim 21, wherein OR8 is selective towards 1-octen-3-ol.

23. A single-molecule field-effect transistor (smFET) device comprising one carbon nanotube (CNT) and a capture probe covalently coupled thereto via a linker moiety, wherein the capture probe comprises at least a mosquito-derived indolergic odorant receptor (OR) configured to bind or associate to at least one volatile organic compound (VOC), wherein the smFET further comprises at least one electrode assembly disposed proximate opposing ends of the one CNT to electrically couple the one CNT to a substrate onto which the smFET is disposed, wherein the capture probe is not DNA or a nucleotide.

24. A method for detecting or sensing presence of at least one volatile organic compound (VOC), present in a sample, the method comprising contacting a bioelectronic sensor comprising a single carbon nanotube (CNT) to which a single mosquito-derived indolergic odorant receptor (OR) is immobilized via a linker moiety, under conditions permitting association of the VOC to said receptor, wherein association of the VOC to said receptor causes a measurable electric field effect.

25. The method according to claim 24, wherein the sensor is a single-molecule field-effect transistor (smFET) device comprising one CNT and a capture probe covalently coupled thereto, wherein the capture probe comprises at least one receptor configured to bind or associate to at least one VOC, wherein the smFET further comprises at least one electrode assembly disposed proximate opposing ends of the one CNT to electrically couple the one CNT to a substrate onto which the smFET is disposed, wherein the capture probe is not DNA or a nucleotide.

26. The method of claim 24, wherein the single insect receptor derived from mosquitos or flies is a membrane bound receptor, said receptor comprising a membrane containing said membrane bound receptor.

* * * * *